(12) United States Patent
Diamond et al.

(10) Patent No.: US 8,580,773 B2
(45) Date of Patent: Nov. 12, 2013

(54) SMALL-MOLECULE INHIBITORS OF THE ANDROGEN RECEPTOR

(71) Applicant: The Regents of the University of California, Oakland, CA (US)

(72) Inventors: Marc I. Diamond, San Francisco, CA (US); Jeremy O. Jones, San Francisco, CA (US); Adam R. Renslo, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/706,647

(22) Filed: Dec. 6, 2012

(65) Prior Publication Data
US 2013/0096095 A1 Apr. 18, 2013

Related U.S. Application Data

(62) Division of application No. 12/989,389, filed as application No. PCT/US2009/041715 on Apr. 24, 2009, now Pat. No. 8,354,538.

(60) Provisional application No. 61/047,559, filed on Apr. 24, 2008.

(51) Int. Cl.
*A61K 31/4709* (2006.01)
*A61K 31/496* (2006.01)
*A61K 31/473* (2006.01)
*A61K 31/585* (2006.01)
*A61K 45/06* (2006.01)
*C07D 401/06* (2006.01)

(52) U.S. Cl.
USPC ....... 514/171; 514/254.07; 514/284; 514/314

(58) Field of Classification Search
None
See application file for complete search history.

(56) References Cited

U.S. PATENT DOCUMENTS

| 3,821,228 | A | 6/1974 | Richards |
| 3,983,121 | A | 9/1976 | Murthi |
| 6,143,895 | A | 11/2000 | Pei |
| 7,037,919 | B1 | 5/2006 | Hanada |
| 7,696,227 | B2 | 4/2010 | Diamond |
| 2003/0162777 | A1 | 8/2003 | Leonardi et al. |
| 2006/0148834 | A1 | 7/2006 | Xu |
| 2007/0254875 | A1 | 11/2007 | Zhi |
| 2007/0269405 | A1 | 11/2007 | Wang |

FOREIGN PATENT DOCUMENTS

| DE | 2421382 | 11/1975 |
| EP | 1325914 | 7/2003 |
| WO | WO 03/031436 | 4/2003 |
| WO | WO 2006/078754 | 7/2006 |
| WO | WO 2007/117466 | 10/2007 |

OTHER PUBLICATIONS

European Search Report dated May 24, 2012, issued in European Patent Application No. 09735196.9.
International Search Report and Written Opinion dated Jul. 14, 2008, issued in International Patent Application No. PCT/US08/60107.
Rao, V. Aruna et al., "Agents Acting on the Central Nervous System, XIII," 1970, Journal of Medical Chemistry, vol. 13, pp. 516-522. XP002292998.
Hieronymus, Haley, et al., "Gene expression signature-based chemical genomic prediction identifies a novel class of HSP90 pathway modulators," Cancer Cell, 2006, vol. 10, pp. 321-330.
Vippagunta et al., Crystalline solids, 48 Adv. Drug Delivery Rev. 3-26 (2001).
Rautio et al., Prodrugs: Design and Clinical Applications, 7 Nat. Rev. Drugs Dis., 255-70(2008).

*Primary Examiner* — Janet Andres
*Assistant Examiner* — Timothy R Rozof
(74) *Attorney, Agent, or Firm* — Kilpatrick Townsend & Stockton LLP.

(57) ABSTRACT

The present invention provides tetrahydropyrvinium (THP), derivatives thereof, benzoxazole compounds, and derivatives thereof. The present invention provides a method of using tetrahydropyrvinium (THP), derivatives thereof, benzoxazole compounds, and derivatives thereof.

17 Claims, 18 Drawing Sheets

Culture cells with test compounds
↓
HEK293/C-AR-Y
LAPC4/C-AR-Y
HEK293/AR/MMTV-Luc
↓
Screen in Duplicate
FRET Assay
Transcription Assay
↓
Select compounds that function similarly in both trials to reduce signal more than specified SDs
↓
Re-evaluate top 50 hits from each assay with dose-response
↓
Cross-test hits in each primary assay system

*Fig. 1*

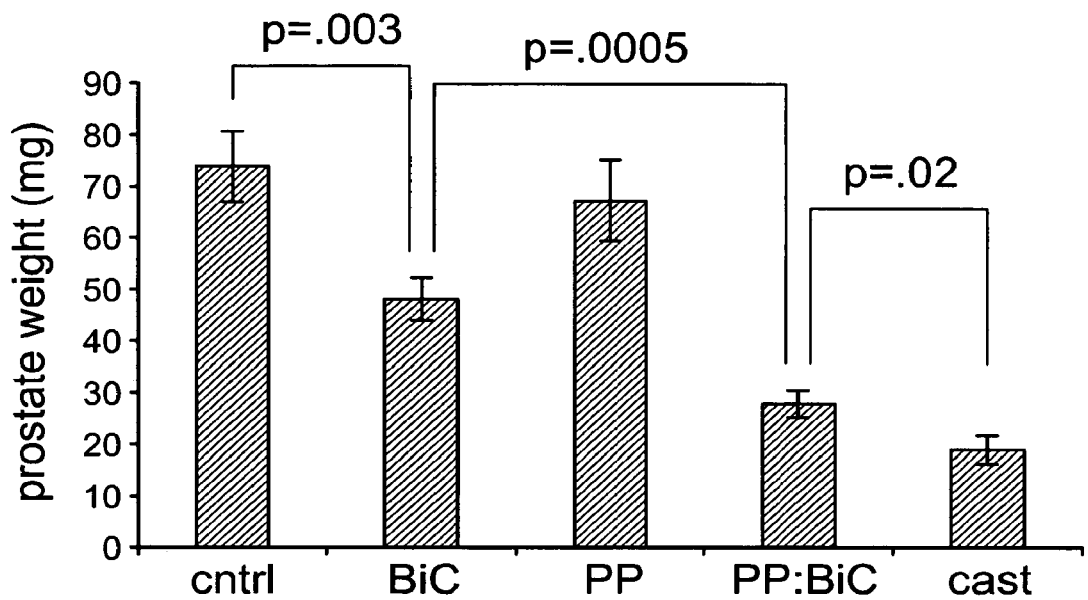
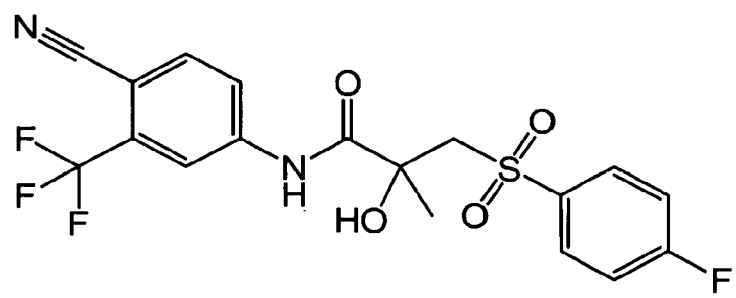
Bicalutamide (BiC)
Fig. 7

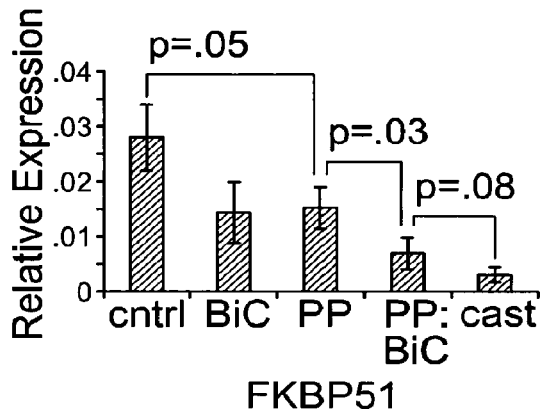
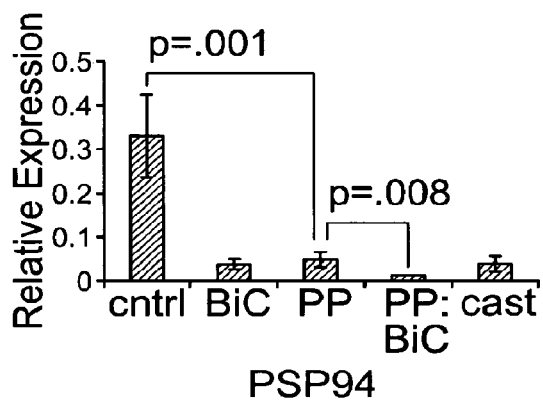
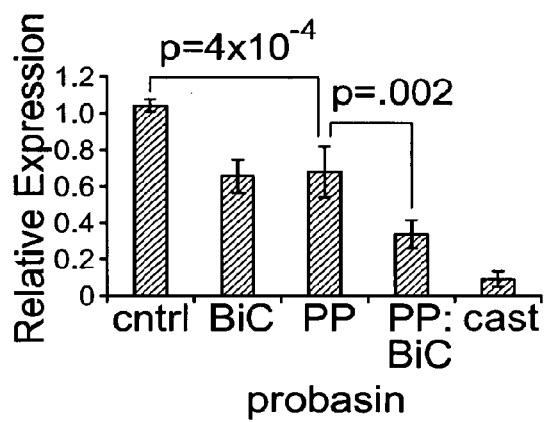
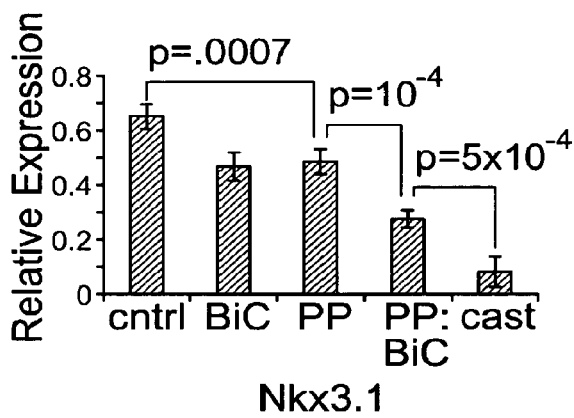
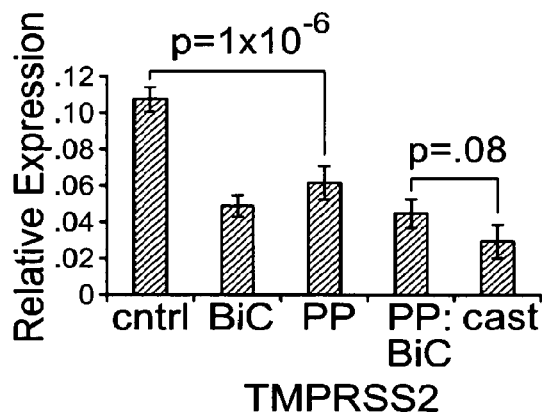
Fig. 8

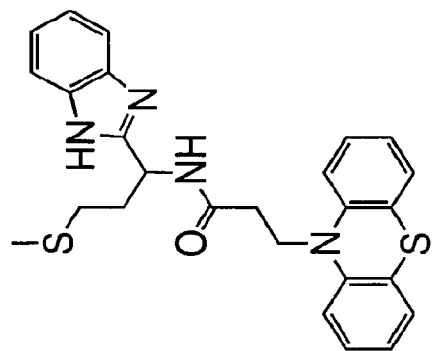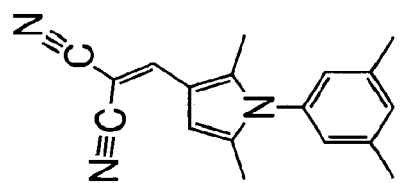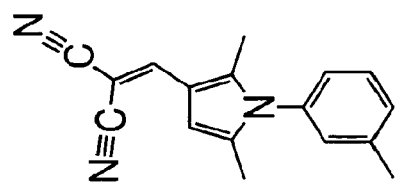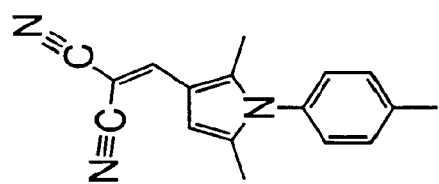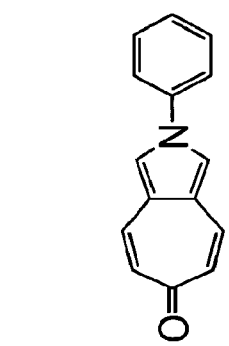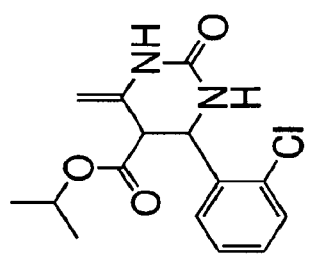
Fig. 9

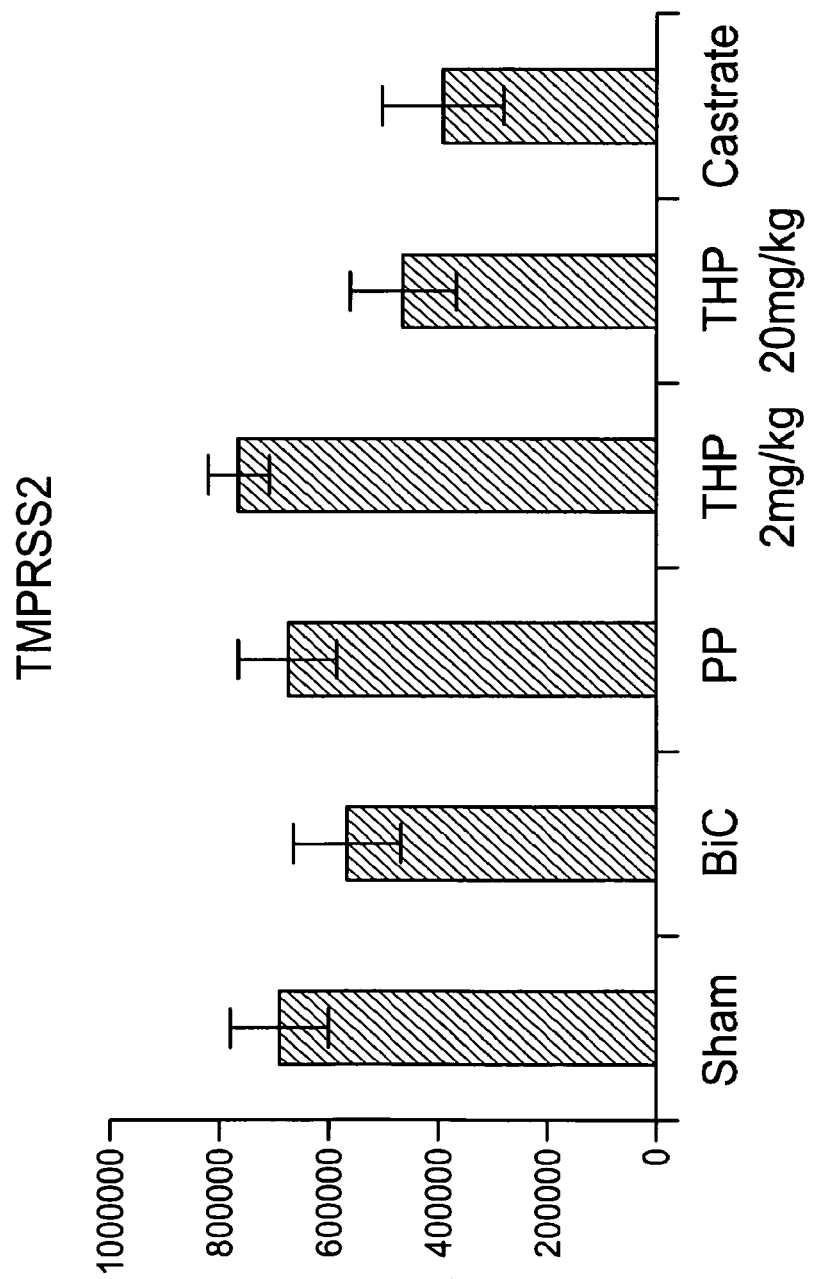
Fig. 13 (Sheet 1)

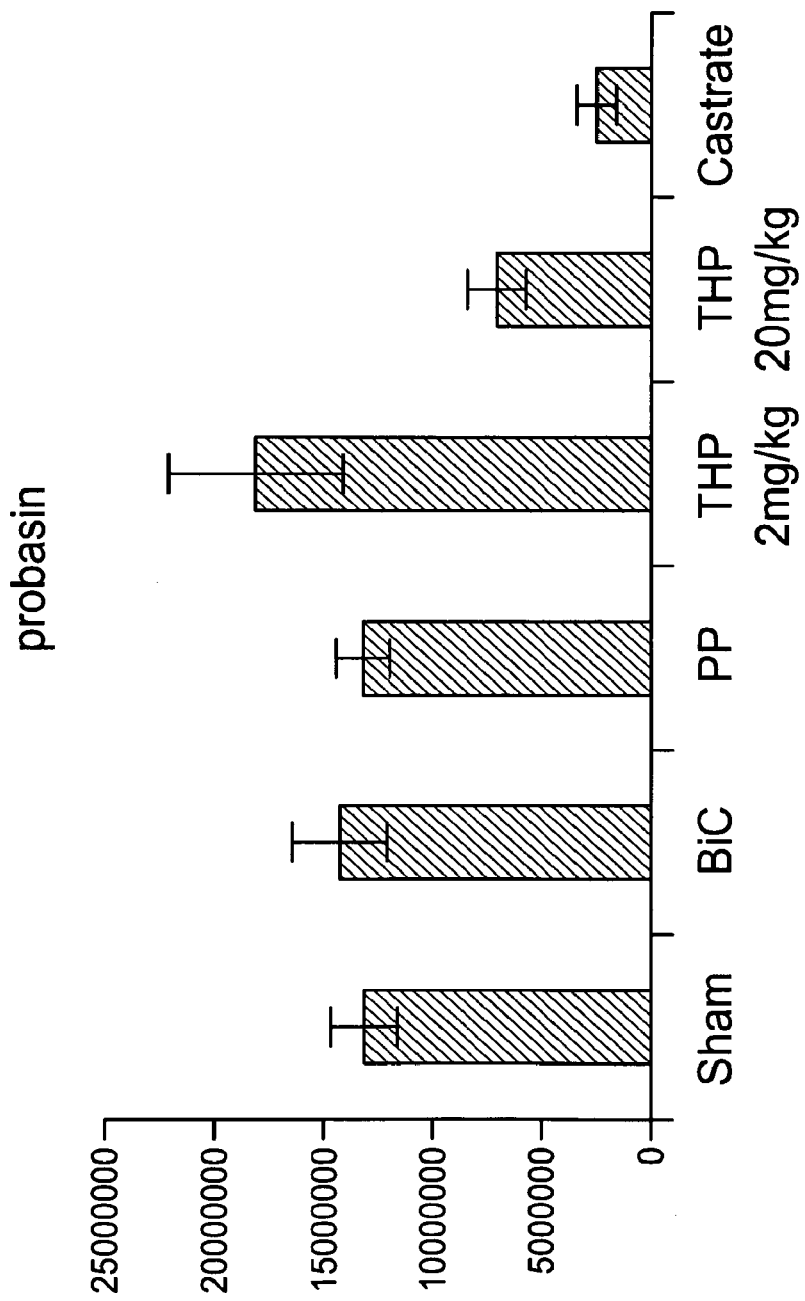
Fig. 13 (Sheet 2)

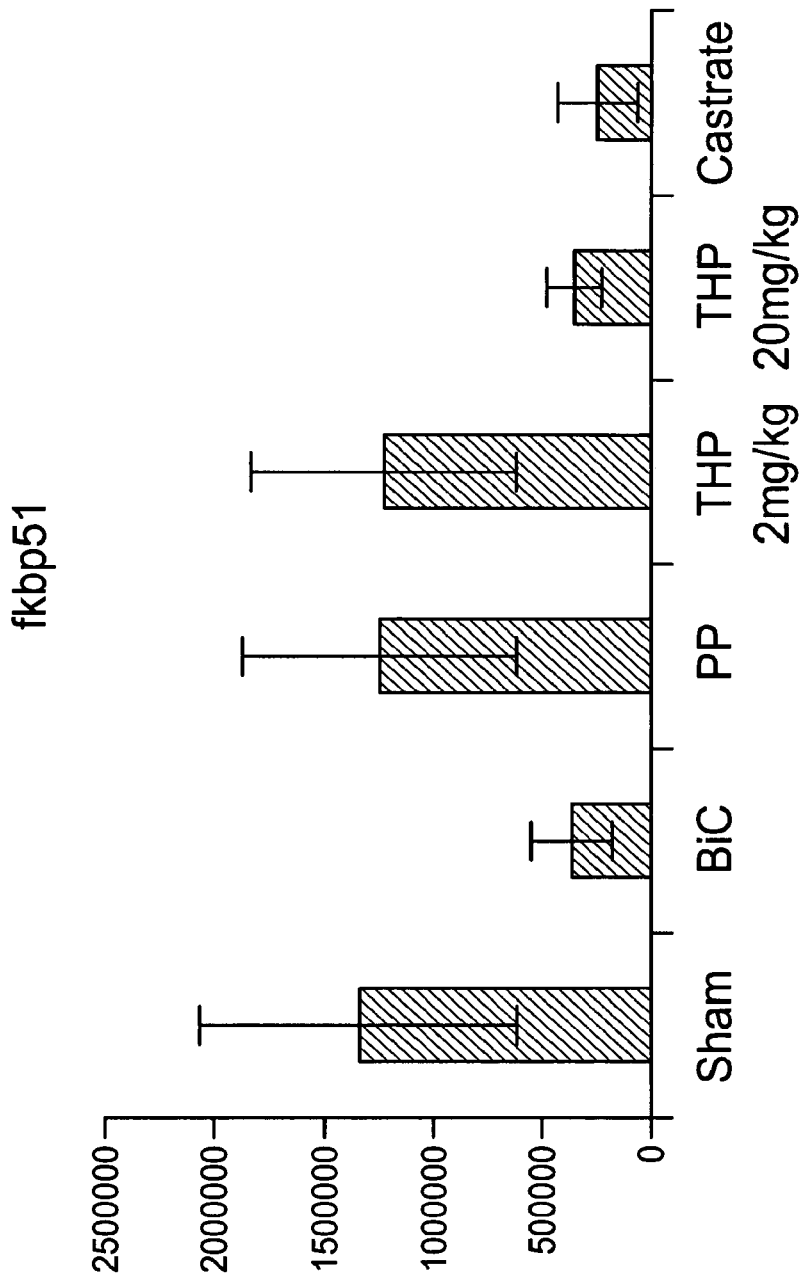
Fig. 13 (Sheet 3)

| Drug combination | Expected IC$_{50}$ (additive) | Actual IC$_{50}$ | CI$_{50}$ (Synergy) |
|---|---|---|---|
| THP:BiC (1:30) | 5.6 nM | 1.8 nM | 0.19 |

Fig. 15

| Compound | LAPC4 |
|---|---|
| THP | +++ |
| SHP | ++ |

Activity

+ = >1 mM
++ = >100 nM
+++ = <100 nM

SHP

SMALL-MOLECULE INHIBITORS OF THE ANDROGEN RECEPTOR

CROSS REFERENCE TO RELATED APPLICATIONS

The present application is a divisional application of U.S. Ser. No. 12/989,389, filed May 13, 2011, which entered the U.S. under 35 U.S.C. §371 from PCT/US2009/041715, filed Apr. 24, 2009, which claims priority to U.S. Ser. No. 61/047,559, filed Apr. 24, 2008, herein incorporated by reference in their entirety.

STATEMENT AS TO RIGHTS TO INVENTIONS MADE UNDER FEDERALLY SPONSORED RESEARCH OR DEVELOPMENT

Not applicable.

REFERENCE TO A SEQUENCE LISTING, A TABLE, OR A COMPUTER PROGRAM LISTING APPENDIX SUBMITTED ON A COMPACT DISK

Not applicable.

BACKGROUND OF THE INVENTION

Prostate cancer (PCa) is a leading cause of cancer morbidity and mortality in men, and the androgen receptor (AR) is the primary therapeutic target. In early PCa, anti-androgen therapy (AAT) is almost universally effective. This consists of one or more combinations of GnRH agonists (to suppress pituitary signaling), aromatase inhibitors (to decrease androgen production), and competitive AR antagonists (to block AR directly) such as hydroxy-flutamide (OH—F) or bicalutamide (BiC). This strategy usually works for several years, but over time tumor cells evolve mechanisms for continued growth under these conditions of androgen depletion. Most recurrent, or hormone-refractory prostate cancer (HRPC) is nonetheless dependent on AR-mediated signaling. This can include upregulation of AR protein expression levels, acquisition of mutations within AR that increase its activity in response to alternative hormones (including antagonists), or upregulation of co-activator proteins that augment AR activity. Thus, it is likely that new approaches to block AR activity could significantly extend or increase the effectiveness of AAT. This could consist of better competitive antagonists, and considerable efforts from pharmaceutical companies are already being brought to bear on this approach. This implies that novel anti-androgens might have considerable utility in the treatment of both primary and recurrent PCa. Such anti-androgens might not be competitive antagonists that directly bind AR, and could conceivably function via inhibition of downstream events in AR signaling. Accordingly, there is a need for novel, potent anti-androgens. Surprisingly, this invention meets this, and other, needs.

BRIEF SUMMARY OF THE INVENTION

In one embodiment, the present invention provides compounds of Formula I:

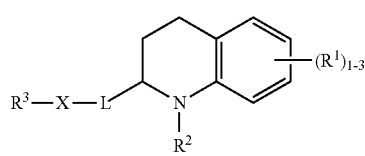

(I)

wherein each $R^1$ is independently hydrogen, $C_{1-6}$ alkyl, $C_{2-6}$ alkenyl, $C_{2-6}$ alkynyl, $C_{1-6}$ alkoxy, —$OR^4$, —$SR^4$, —$NR^4R^5$, cycloalkyl, heterocycloalkyl, aryl or heteroaryl. $R^2$ is hydrogen, $C_{1-6}$ alkyl, $C_{1-6}$ alkyl-OH, $C_{2-6}$ alkenyl or $C_{2-6}$ alkynyl. $R^3$ is cycloalkyl, heterocycloalkyl, aryl or heteroaryl, optionally substituted with from 1 to 3 $R^6$ groups. $R^4$ and $R^5$ are each independently hydrogen, $C_{1-6}$ alkyl, $C_{2-6}$ alkenyl or $C_{2-6}$ alkynyl. Alternatively $R^4$ and $R^5$ are combined with the nitrogen to which they are attached to form a heterocyclic ring having from 5 to 7 ring members and from 1 to 3 heteroatoms each independently N, O or S. Each $R^6$ is independently H, $C_{1-6}$ alkyl, $C_{2-6}$ alkenyl, $C_{2-6}$ alkynyl or $C_{1-6}$ alkoxy. L is a linker of $C_{1-6}$ alkylene, $C_{2-6}$ alkenylene, $C_{2-6}$ alkynylene or $C_{3-6}$ cycloalkylene. X is —$N(R^7)$—, an aryl ring having 6-10 ring members and a heteroaryl ring having from 5 to 6 ring members and from 1 to 3 heteroatoms each independently N, O or S, wherein the aryl and the heteroaryl ring are each optionally substituted with from 1 to 3 $R^8$ groups. $R^7$ is H, $C_{1-6}$ alkyl, $C_{2-6}$ alkenyl or $C_{2-6}$ alkynyl. Each $R^8$ is independently H, $C_{1-6}$ alkyl, $C_{2-6}$ alkenyl, $C_{2-6}$ alkynyl or $C_{1-6}$ alkoxy. The compounds of Formula I include the salts, hydrates and prodrugs thereof.

In a second embodiment, the present invention provides compounds of Formula II:

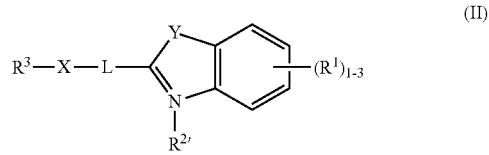

(II)

wherein $R^1$, $R^3$, $R^4$, $R^5$, $R^6$, $R^7$, $R^8$, X and L are as defined above; $R^{2'}$ is an electron pair, hydrogen, $C_{1-6}$ alkyl, $C_{1-6}$ alkyl-OH, $C_{2-6}$ alkenyl or $C_{2-6}$ alkynyl; and Y is O or S. The compounds of Formula II include the salts, hydrates and prodrugs thereof.

In a third embodiment, the present invention provides a pharmaceutical composition including a compound of Formula I and a pharmaceutically acceptable excipient.

In a fourth embodiment, the present invention provides a method of inhibiting an androgen receptor by administering to a patient in need of such treatment, a therapeutically effective amount of a compound of Formula I or Formula II.

In a fifth embodiment, the present invention provides tetrahydropyrvinium (THP), derivatives thereof, benzoxazole compounds, and derivatives thereof.

In a sixth embodiment, the present invention provides a method of using tetrahydropyrvinium (THP), derivatives thereof, benzoxazole compounds, and derivatives thereof.

BRIEF DESCRIPTION OF THE DRAWINGS

FIG. 1. Compound screening strategy. Novel inhibitors of AR conformation change were discovered by creating a HEK-293 (ATCC CRL-1573)-derived cell line stably expressing a CFP N-terminal and YFP C-terminal tagged AR vector that has been previously used to measure conformation change by FRET. C-AR-Y was stably expressed in either LAPC4 or HEK293 cell lines; in parallel, HEK293 cells were transfected with native AR along with MMTV-luciferase. Cells were cultured in the presence or absence of 10 nM dihydrotestosterone (DHT) and one of 1040 FDA-approved drugs. The screen was performed in duplicate for each condition, and the top 50 compounds with activities in both trials were selected. Each of the top compounds was evaluated in detail with a dose-response study, and the "validated" compounds were compared across all assays. The validated hits accounted for approximately 40% of the hits initially identified for each screen.

FIG. 7. PP synergistically reduces prostate size in mice. Cohorts of nine male mice were treated with PO gavage of BiC (100 mg/kg), IP injection of PP (1 mg/kg), or the combination for four weeks. As a positive control, nine mice were treated with castration for four weeks. Prostate glands were harvested and wet weights determined. PP alone did not significantly reduce prostate size. BiC treatment significantly reduced prostate weight by 35%, and the combination of PP:BiC reduced the weight by 63% (p<0.0005, t-test), implying a synergistic effect of PP. cntrl: untreated mice; BiC: bicalutamide; PP: pyrvinium pamoate; cast: castrated. Error bars represent the standard error of the mean (S.E.M.).

FIG. 8. PP suppresses androgen-dependent gene expression in the prostate, and augments BiC activity. Total RNA was extracted from prostate glands of cohorts of 9 mice used to test PP in vivo. qRT-PCR was performed to assess gene expression levels of five androgen-induced genes. Gene expression levels are expressed relative to RPL19, an androgen-unresponsive gene. PP significantly suppressed gene expression in all cases, and augmented the effects of BiC, with one exception (TMPRSS2), which may have been maximally suppressed by each treatment alone. cntrl: untreated; BiC: bicalutamide; PP: pyrvinium pamoate; cast: castrated.

FIG. 9. Inhibitors of the androgen receptor.

FIG. 13. Quantitative PCR of androgen-regulated genes TMPRSS2 probasin, and fkbp51.

FIG. 15. Synergistic effects of THP+BiC against AR transcription in LAPC4 cells.

DETAILED DESCRIPTION OF THE INVENTION

I. Introduction

Figure 2:
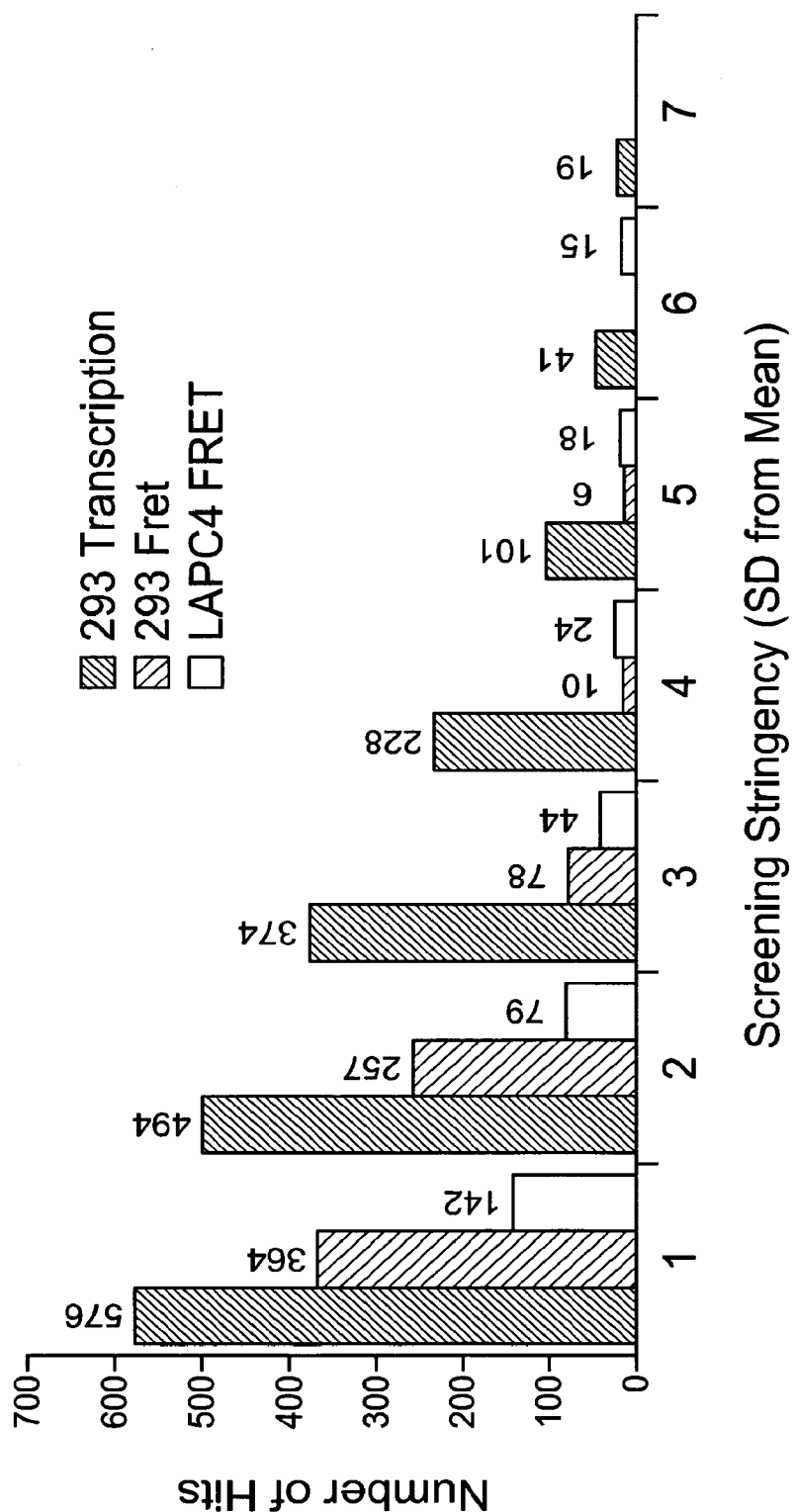
FIG. 2. Analysis of hits. 1040 FDA-approved drugs were tested in three different assays, a transcription-based assay using HEK293 cells expressing MMTV-luciferase, conformation-based assays using HEK293/C-AR-Y stable cells, and LAPC4/C-AR-Y stable cells. Fewer compounds affected AR conformational change vs. transcriptional output. LAPC4 cells were the least sensitive to test compounds. High selectivity (<50 hits) was observed for the transcription assay when the cutoff was set between 5 and 6 standard deviations (SD) from the mean (as determined by multiple replicates of cells treated only with DHT). Similar selectivity was observed for the HEK293/C-AR-Y cells between 3 and 4 SD, whereas in the LAPC4/C-AR-Y cells such effects were observed between 2 and 3 SD from the mean. The transcriptional assay used in the screen had a Z-factor=0.6, vs. 0.6 for the LAPC4 FRET assay and 0.5 for the HEK293 FRET assay (Zhang, J. H., T. D. Chung, and K. R. Oldenburg, *A Simple Statistical Parameter for Use in Evaluation and Validation of High Throughput Screening Assays*. J Biomol Screen, 1999. 4(2): p. 67-73).

The present invention provides a method of inhibiting an androgen receptor by administering to a patient in need of such treatment, a therapeutically effective amount of a compound of Formula I:

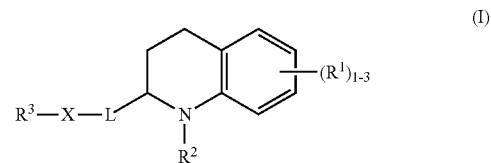

or a compound of Formula II:

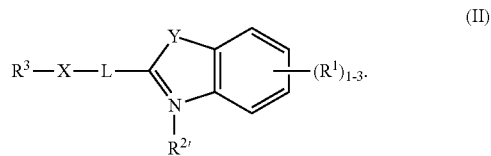

The compounds of the present invention are believed to inhibit folding of the androgen receptor, thus inhibiting receptor activation. The compounds of the present invention can be used to treat any disease involving folding of the androgen receptor. Patients in need of such treatment often suffer from prostate cancer, including primary and hormone refractory prostate cancer, ovarian cancer, hepatocellular carcinoma, acne vulgaris, endometriosis, acanthosis nigricans, hypertrichosis, breast cancer, precocious puberty, polycystic ovary syndrome, benign prostatic hyperplasia, alopecia (such as androgen-dependent alopecia), hirsutism and hypersexuality/paraphilia.

The compounds of the present invention can be used to inhibit other nuclear receptors and treat associated disease states. Receptor activation of PPARγ can be inhibited using the compounds of the present invention, thereby treating disease states such as insulin resistance, diabetes and lipodystrophy, including cholesterol disorders. The compounds of the present invention are useful in treating disease states associated with estrogen receptor α and β, such as breast, colon, ovarian and endometrial cancers, as well as in metabolic regulation. Other disease states that can be treated with the compounds of the present invention include those associated with the thyroid hormone receptor, such as thyroid and cardiac disorders. Such compounds can also be used to augment the inhibition of the glucocorticoid receptor, which is used for immune suppression in a multitude of diseases. The compounds of the present invention can also inhibit the progesterone receptor, resulting in termination of a pregnancy.

II. Definitions

As used herein, "administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

The term "lower" referred to above and hereinafter in connection with organic radicals or compounds respectively defines a compound or radical which can be branched or unbranched with up to and including 7, preferably up to and including 4 and (as unbranched) one or two carbon atoms.

Substituents for the alkyl and heteroalkyl radicals (including those groups often referred to as alkylene, alkenyl, heteroalkyl, heteroalkenyl, alkynyl, cycloalkyl, heterocycloalkyl, cycloalkenyl, and heterocycloalkenyl) can be a variety of groups selected from: R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2 m'+1), where m' is the total number of carbon atoms in such radical. R', R" and R'" each independently refer to hydrogen, unsubstituted ($C_1$-$C_8$) alkyl and heteroalkyl, unsubstituted aryl, aryl substituted with 1-3 halogens, unsubstituted alkyl, alkoxy or thioalkoxy groups, or aryl-($C_1$-$C_4$) alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that substituted alkyl is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, substituted alkyl and heteroalkyl groups have from 1 to 4 substituents; more preferably, 1, 2 or 3 substituents. Exceptions are those perhalo alkyl groups (e.g., pentafluoroethyl and the like) which are also preferred and contemplated by the present invention.

Alternatively, R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl.

As used herein, the term "alkylene" refers to an alkyl group linking at least two other groups, i.e. a divalent hydrocarbon radical of 1 to 6 carbon atoms. As for alkyl, the alkylene group can be straight or branched. For instance, a straight chain alkylene can be the bivalent radical of —(CH$_2$)$_n$—, where n is 1, 2, 3, 4, 5 or 6. Alkylene groups include, but are not limited to, methylene, ethylene, propylene, butylene, pentylene and hexylene. Similarly, "alkenylene," "alkynylene" and "cycloalkylene" are divalent radicals of alkenyl, alkynyl and cycloalkyl (see within).

As used herein, the term "alkenyl" refers to either a straight chain or branched hydrocarbon of 2 to 6 carbon atoms, having at least one carbon-carbon double bond. Examples of alkenyl groups include, but are not limited to, vinyl, propenyl, isopropenyl, butenyl, isobutenyl, butadienyl, pentenyl or hexadienyl.

As used herein, the term "alkynyl" refers to either a straight chain or branched hydrocarbon of 2 to 6 carbon atoms, having at least one carbon-carbon triple bond. Examples of alkynyl groups include, but are not limited to, acetylenyl, propynyl or butynyl.

As used herein, the term "alkoxy" refers to alkyl with the inclusion of an oxygen atom, for example, methoxy, ethoxy, etc. "Halo-substituted-alkoxy" is as defined for alkoxy wherein some or all of the hydrogen atoms are replaced with halogen atoms. For example, halo-substituted-alkoxy includes trifluoromethoxy, etc.

As used herein, the term "cycloalkyl" refers to a saturated or partially unsaturated, monocyclic, fused bicyclic, or bridged polycyclic ring assembly containing from 3 to 12 ring atoms (i.e., ring members; that is, atoms directly connected to form the framework of the ring, such as the six carbons in a cyclohexyl group), or the number of atoms indicated For example, $C_{3-8}$ cycloalkyl includes cyclopropyl, cyclobutyl, cyclopentyl, cyclohexyl, and up to cyclooctyl.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycloalkyl includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene"

means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy, and oxy-$C_2$-$C_3$-alkylene; or 1- or 2-naphthyl; or 1- or 2-phenanthrenyl. "Alkylenedioxy" is a divalent substitute attached to two adjacent carbon atoms of phenyl, e.g., methylenedioxy or ethylenedioxy. "Oxy-$C_2$-$C_3$-alkylene" is also a divalent substituent attached to two adjacent carbon atoms of phenyl, e.g., oxyethylene or oxypropylene. An example for oxy-$C_2$-$C_3$-alkylene-phenyl is 2,3-dihydrobenzofuran-5-yl.

Preferred aryl groups include naphthyl, phenyl, or phenyl mono- or disubstituted by alkoxy, phenyl, halogen, alkyl, or trifluoromethyl; more preferably, phenyl or phenyl mono- or disubstituted by alkoxy, halogen or trifluoromethyl; and, phenyl.

Examples of substituted phenyl groups as R are, e.g., 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl.

Similarly, other substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$) alkyl, in a number ranging from zero to the total number of open valences on the aromatic ring system; and where R', R" and R'" are independently selected from hydrogen, ($C_1$-$C_8$) alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

As used herein, the term "heteroaryl" refers to a monocyclic or fused bicyclic or tricyclic aromatic ring assembly containing 5 to 16 ring atoms (i.e., ring members; that is, atoms directly connected to form the framework of the ring, such as the five carbons and one nitrogen in a 2-pyridyl group), where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by alkyl, nitro, or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted by alkyl, nitro, or halogen.

As used herein, the term "androgen receptor" refers to an intracellular steroid receptor of the nuclear receptor superfamily that specifically binds androgens such as testosterone and dihydrotestosterone.

As used herein, the term "anti-androgen" refers to a group of hormone receptor antagonist compounds that are capable of preventing or inhibiting the biologic effects of androgens, male sex hormones, on normally responsive tissues in the body. Antiandrogens usually work by blocking the appropriate receptors, competing for binding sites on intracellular receptors, and obstructing androgen signaling pathways. As well as the compounds of Formula I and II, anti-androgens include, but are not limited to, coumarins, bicalutamide, flutamide, hydroxyflutamide, nilutamide, spionolactone, cyproterone acetate, ketoconazole, finasteride, dutasteride, harman, norharman, harmine, harmaline, tetrahydroharmine, harmol, harmalol, ethyl harmol, n-butyl harmol and other beta-carboline derivatives.

Antiandrogens are often indicated to treat severe male sexual disorders, such as hypersexuality (excessive sexual desire) and sexual deviation, specifically paraphilias, as well as use as an antineoplastic agent and palliative, adjuvant or neoadjuvant hormonal therapy in prostate cancer. Antiandrogens can also be used for treatment of benign prostatic hyperplasia (prostate enlargement), acne vulgaris, androgenetic alopecia (male pattern baldness), and hirsutism (excessive hair growth). Anti-androgens are also occasionally used as a male contraceptive agent, to purposefully prevent or counteract masculinisation in the case of transgender women undergoing gender reassignment therapy, and to prevent the symptoms associated with reduced testosterone, such as hot flashes, following castration. Other conditions treatable with an anti-androgen are prostate cancer, including primary and hormone refractory prostate cancer, ovarian cancer, hepatocellular carcinoma, acne vulgaris, endometriosis, acanthosis nigricans, hypertrichosis, breast cancer, precocious puberty, polycystic ovary syndrome, benign prostatic hyperplasia, alopecia (such as androgen-dependent alopecia), hirsutism and hypersexuality/paraphilia.

As used herein, the term "a combination of active agents" refers to a composition of at least two or more active agents.

As used herein, the term "counterion" refers to the ion that accompanies an ionic species in order to maintain electronic neutrality. Counterions can be atomic, such as fluoride, chloride, bromide, iodide, or metallic counterions. Counterions can also be molecular, such as acetate, succinate, maleate and embonate (pamoate). Counterions can be positively or negatively charged. Counterions of the present invention are negatively charged. In addition, counterions can have a charge greater than 1, such as 2 or more. One of skill in the art will appreciate that other counterions are useful in the present invention.

As used herein, the term "hormonal therapy" refers to the use of hormones in medical treatment, as well as the inhibition of hormone production, such as the use of direct competitors to hormones, such as antiandrogens.

As used herein, the term "hydrate" refers to a compound that is complexed to at least one water molecule. The compounds of the present invention can be complexed with from 1 to 10 water molecules.

As used herein, the term "inhibiting" refers to a compound that partially or fully prohibits or a method of partially or fully prohibiting a specific action or function.

As used herein, the term "LnRH agonist" refers to a compound or biological molecule that binds to the luteinizing releasing-hormone receptor.

As used herein, the term "patient in need" refers to a patient suffering from prostate cancer, polycystic ovary syndrome, benign prostatic hyperplasia, alopecia and hirsutism. Other conditions that a patient in need suffers from include, but are not limited to, ovarian cancer, hepatocellular carcinoma, acne vulgaris, endometriosis, acanthosis nigricans, hypertrichosis, breast cancer, precocious puberty and hypersexuality/paraphilia. Patients suffering from other conditions treatable with anti-androgens are also treatable with the methods of the present invention. Patients treatable using the methods of the present invention are animals such as mammals, including, but not limited to, primates (e.g., humans), cows, sheep, goats, horses, dogs, cats, rabbits, rats, mice and the like. In certain embodiments, the patient is a human.

As used herein, the term "prodrug" refers to covalently bonded carriers which are capable of releasing the active agent of the methods of the present invention, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of the active agents of the present invention include active agents wherein a hydroxy, amidino, guanidino, amino, carboxylic or a similar group is modified.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the basic compounds of the present invention are salts formed with acids, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

III. Method of Inhibiting an Androgen Receptor

Figure 10:
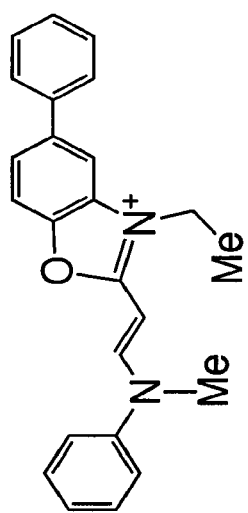
FIG. 10. Inhibitors of the androgen receptor.

The present invention provides a method of inhibiting an androgen receptor by administering to a patient in need of such treatment, a therapeutically effective amount of a compound of Formula I, Formula II, or compounds shown in FIG. 9 and FIG. 10. Compounds useful in the methods of the present invention include compounds of Formula I:

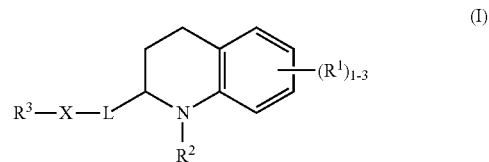

and compounds of Formula II:

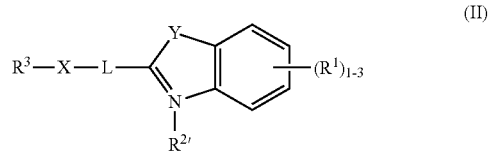

wherein each $R^1$ is independently hydrogen, $C_{1-6}$ alkyl, $C_{2-6}$ alkenyl, $C_{2-6}$ alkynyl, $C_{1-6}$ alkoxy, $-OR^4$, $-SR^4$, $-NR^4R^5$, cycloalkyl, heterocycloalkyl, aryl or heteroaryl. $R^2$ is hydrogen, $C_{1-6}$ alkyl, $C_{1-6}$ alkyl-OH, $C_{2-6}$ alkenyl or $C_{2-6}$ alkynyl. $R^{2'}$ is an electron pair, hydrogen, $C_{1-6}$ alkyl, $C_{1-6}$ alkyl-OH, $C_{2-6}$ alkenyl or $C_{2-6}$ alkynyl. $R^3$ is cycloalkyl, heterocycloalkyl, aryl or heteroaryl, optionally substituted with from 1 to 3 $R^6$ groups. $R^4$ and $R^5$ are each independently hydrogen, $C_{1-6}$ alkyl, $C_{2-6}$ alkenyl or $C_{2-6}$ alkynyl. Alternatively $R^4$ and $R^5$ are combined with the nitrogen to which they are attached to form a heterocyclic ring having from 5 to 7 ring members and from 1 to 3 heteroatoms each independently N, O or S. Each $R^6$ is independently H, $C_{1-6}$ alkyl, $C_{2-6}$ alkenyl, $C_{2-6}$ alkynyl or $C_{1-6}$ alkoxy. L is a linker of $C_{1-6}$ alkylene, $C_{2-6}$ alkenylene, $C_{2-6}$ alkynylene or $C_{3-6}$ cycloalkylene. X is —N($R^7$)—, an aryl ring having 6-10 ring members and a heteroaryl ring having from 5 to 6 ring members and from 1 to 3 heteroatoms each independently N, O or S, wherein the aryl and the heteroaryl ring are each optionally substituted with from 1 to 3 $R^8$ groups. $R^7$ is H, $C_{1-6}$ alkyl, $C_{1-6}$ alkenyl or $C_{2-6}$ alkynyl. Each $R^8$ is independently H, $C_{1-6}$ alkyl, $C_{2-6}$ alkenyl, $C_{2-6}$ alkynyl or $C_{1-6}$ alkoxy. Y is O or S. The compounds of Formulas I and II include the salts, hydrates and prodrugs thereof. By administering the compound of Formula I, the method inhibits the androgen receptor.

Some of the compounds of Formulas I and II are already known. Other compounds of Formulas I and II are novel compounds. The compounds of Formulas I and II can be combined with other anti-androgen compounds such as coumarins, bicalutamide, flutamide, hydroxyflutamide, nilutamide, spionolactone, cyproterone acetate, ketoconazole, finasteride, dutasteride, harman, harmine, harmaline, tetrahydroharmine, harmol, harmalol, harmine acid, harmine acid methyl ester, harmilinic acid, harmanamide, acetylnorharmine, ethyl harmol, n-butyl harmol and other beta-carboline derivatives.

The compounds of the present invention are believed to inhibit folding of the androgen receptor, thus inhibiting receptor activation. Patients in need of such treatment often suffer from prostate cancer, including primary and hormone refractory prostate cancer, ovarian cancer, hepatocellular carcinoma, acne vulgaris, endometriosis, acanthosis nigricans, hypertrichosis, breast cancer, precocious puberty, polycystic ovary syndrome, benign prostatic hyperplasia, alopecia (such as androgen-dependent alopecia), hirsutism and hypersexuality/paraphilia. Other disease states can be treated using the methods of the present invention.

The compounds of the present invention are believed to inhibit folding of the androgen receptor, thus inhibiting receptor activation. Patients in need of such treatment often suffer from prostate cancer, including primary and hormone refractory prostate cancer, ovarian cancer, hepatocellular carcinoma, acne vulgaris, endometriosis, acanthosis nigricans, hypertrichosis, breast cancer, precocious puberty, polycystic ovary syndrome, benign prostatic hyperplasia, alopecia (such as androgen-dependent alopecia), hirsutism and hypersexuality/paraphilia. Other disease states can be treated using the methods of the present invention.

In another embodiment, the method of the present invention treats alopecia by topical administration of a compound or composition of the present invention.

In other embodiments, the compounds of Formula I and Formula II are administered with a course of hormonal therapy, where the compound for hormonal therapy is an anti-androgen or a LnRH agonist. In some embodiments, the compounds are administered separately. In other embodiments, the compounds are admixed. In some other embodiments, the compounds are administered at the same time. In still other embodiments, the compounds are administered at different times.

In some other embodiments, the compounds of Formula I and Formula II are administered in combination with a therapeutically effective amount of docetaxel (taxol), paclitaxel (taxotere), bicalutamide, flutamide, hydroxyflutamide, nilutamide, spionolactone, cyproterone acetate, ketoconazole, finasteride or dutasteride. In other embodiments, the compounds of Formula I and Formula II are administered in combination with a therapeutically effective amount of a coumarin.

IV. Compounds for Inhibiting an Androgen Receptor

Compounds useful in the present invention are those that inhibit an androgen receptor. Useful compounds can be identified using the assay methods described in the Examples below. These compounds are commercially available or can be synthesized using methods known to those skilled in the art.

In some embodiments, compounds useful in the methods of the present invention include compounds of Formula I:

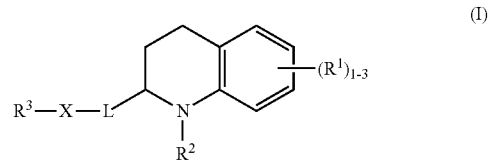

(I)

wherein each $R^1$ is independently hydrogen, $C_{1-6}$ alkyl, $C_{2-6}$ alkenyl, $C_{2-6}$ alkynyl, $C_{1-6}$ alkoxy, —$OR^4$, —$SR^4$, —$NR^4R^5$, cycloalkyl, heterocycloalkyl, aryl or heteroaryl. $R^2$ is hydrogen, $C_{1-6}$ alkyl, $C_{1-6}$ alkyl-OH, $C_{2-6}$ alkenyl or $C_{2-6}$ alkynyl. $R^3$ is cycloalkyl, heterocycloalkyl, aryl or heteroaryl, optionally substituted with from 1 to 3 $R^6$ groups. $R^4$ and $R^5$ are each independently hydrogen, $C_{1-6}$ alkyl, $C_{2-6}$ alkenyl or $C_{2-6}$ alkynyl. Alternatively $R^4$ and $R^5$ are combined with the nitrogen to which they are attached to form a heterocyclic ring having from 5 to 7 ring members and from 1 to 3 heteroatoms each independently N, O or S. Each $R^6$ is independently H, $C_{1-6}$ alkyl, $C_{2-6}$ alkenyl, $C_{2-6}$ alkynyl or $C_{1-6}$ alkoxy. L is a linker of $C_{1-6}$ alkylene, $C_{2-6}$ alkenylene, $C_{2-6}$ alkynylene or $C_{3-6}$ cycloalkylene. X is —N($R^7$)—, an aryl ring having 6-10 ring members and a heteroaryl ring having from 5 to 6 ring members and from 1 to 3 heteroatoms each independently N, O or S, wherein the aryl and the heteroaryl ring are each optionally substituted with from 1 to 3 $R^8$ groups. $R^7$ is H, $C_{1-6}$ alkyl, $C_{2-6}$ alkenyl or $C_{2-6}$ alkynyl. Each $R^8$ is independently H, $C_{1-6}$ alkyl, $C_{2-6}$ alkenyl, $C_{2-6}$ alkynyl or $C_{1-6}$ alkoxy. The compounds of Formula I include the salts, hydrates and prodrugs thereof.

In some embodiments, L is ethylene, ethenylene or cyclopropylene.

In some other embodiments, compounds of the present invention include compounds of Formula Ia:

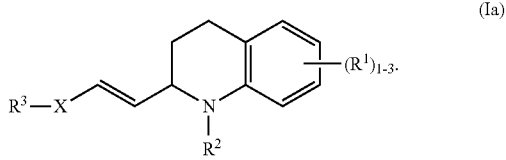

(Ia)

In other embodiments, X is heteroaryl. In still other embodiments, X is pyrrole. In yet other embodiments, X is aryl. In still yet other embodiments, the compound can be:

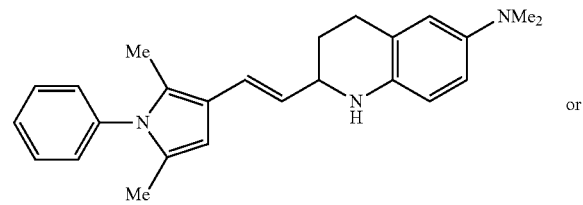

or

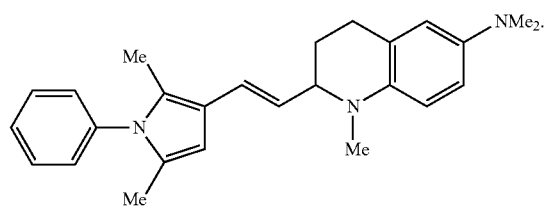

In other embodiments, compounds of the present invention include compounds of the Formula:

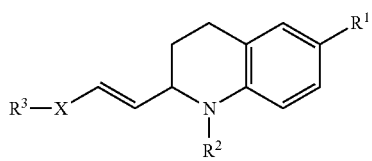

wherein $R^1$ is —$NR^4R^5$, such that $R^4$ and $R^5$ are combined with the nitrogen to which they are attached to form a heterocyclic ring having from 5 to 7 ring members and from 1 to 3 heteroatoms each independently N, O or S. $R^3$ is aryl. X is heteroaryl.

In some embodiments, the compounds of the present invention include compounds of Formula Ib:

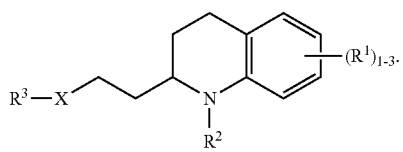

In other embodiments, the compound of Formula Ib is:

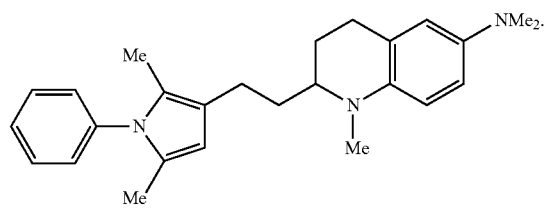 [SMILES: Cc1cc(CCC2CCc3cc(N(C)C)ccc3N2C)c(C)n1-c1ccccc1]

In some other embodiments, the compounds of the present invention include compounds of Formula Ic:

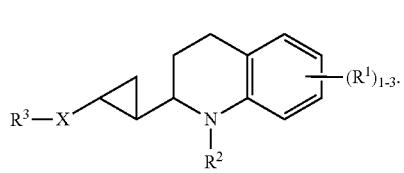

In another embodiment, the compounds of the present invention include compounds of Formula Id:

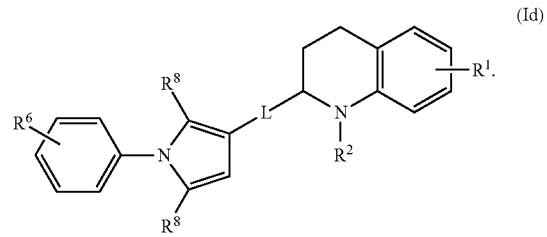

In other embodiments, salt forms of the compounds of Formula I include a counterion of pamoate, chloride, bromide, succinate, maleate or acetate.

In other embodiments, compounds useful in the methods of the present invention include compounds of Formula II:

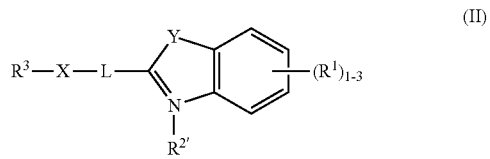

wherein $R^1$, $R^3$, $R^4$, $R^5$, $R^6$, $R^7$, $R^8$, X and L are as defined above; $R^{2'}$ is an electron pair, hydrogen, $C_{1-6}$ alkyl, $C_{1-6}$ alkyl-OH, $C_{2-6}$ alkenyl or $C_{2-6}$ alkynyl; and Y is O or S. The compounds of Formula II include the salts, hydrates and prodrugs thereof.

In some embodiments, the compounds of Formula II include the following:

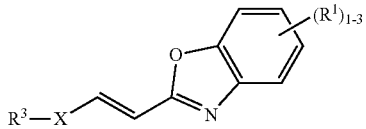

wherein X is aryl or heteroaryl. In other embodiments, the compounds have the following formula:

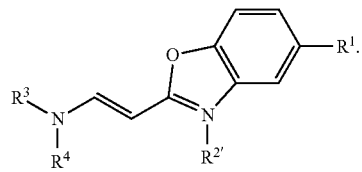

In some other embodiments, le and $R^3$ are both aryl, and le and $R^3$ are both $C_{1-6}$ alkyl. In still other embodiments, the compound is:

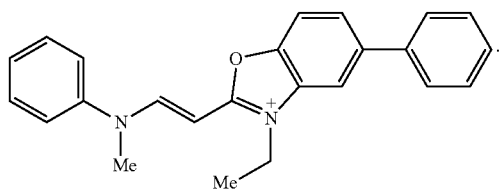

V. Formulations for Inhibiting an Androgen Receptor

The compounds of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 20th ed., 2003, supra). For example, the compounds of the present invention can be prepared and administered in a wide variety of oral, injectable and topical dosage forms. The compounds of the present invention can also be prepared and administered in parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally or topically, e.g., in a liquid or gel form or as a patch.

Accordingly, the present invention also provides pharmaceutical compositions comprising a pharmaceutically acceptable carrier or excipient and one or more compounds of the invention. In some embodiments, the compound can be any of the following:

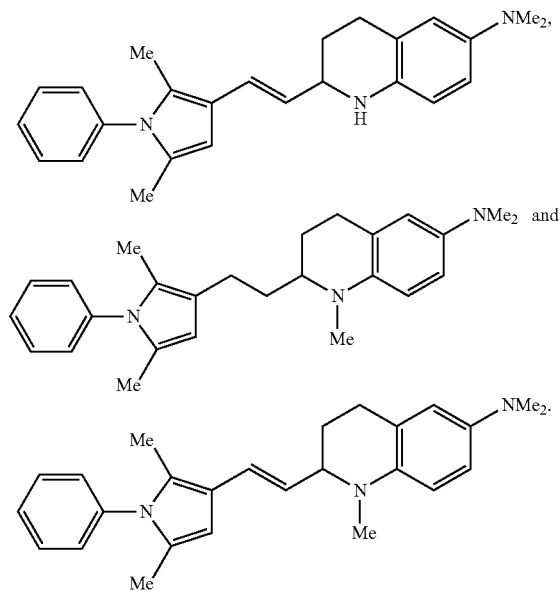

In other embodiments, the compound can be:

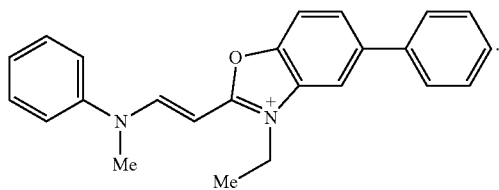

Formulations suitable for administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

For cancer therapy, formulations of the present invention can include a compound of Formulas I or II in combination with a therapeutically effective amount of an anti-androgen or an LnRH agonist. Anti-androgens, as described above, include, but are not limited to, coumarins, bicalutamide, flutamide, hydroxyflutamide, nilutamide, spionolactone, cyproterone acetate, ketoconazole, finasteride, dutasteride, harman, norharman, harmine, harmaline, tetrahydroharmine, harmol, harmalol, ethyl harmol, n-butyl harmol and other beta-carboline derivatives.

In practicing the methods of the present invention, the pharmaceutical compositions can be used alone, or in combination with other therapeutic or diagnostic agents. The additional anticancer drugs used in the combination protocols of the present invention can be formulated separately, or one or more of the anticancer drugs used in the combination protocols can be formulated together, such as in an admixture. Formulations of the present invention can also include combinations of compounds of Formulas I and II. Additional therapeutic agents or diagnostic agents, such as those provided above, can also be formulated in combination with the combination of compounds of Formulas I and II.

VI. Administration to Inhibit an Androgen Receptor

The compounds of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch.

The pharmaceutical compositions can be administered to the patient in a variety of ways, including topically, parenterally, intravenously, intradermally, intramuscularly, colonically, rectally or intraperitoneally. Preferably, the pharmaceutical compositions are administered parenterally, topically, intravenously, intramuscularly or orally.

In practicing the methods of the present invention, the pharmaceutical compositions can be used alone, or in combination with other therapeutic or diagnostic agents. The additional anticancer drugs used in the combination protocols of the present invention can be administered separately or one or more of the anticancer drugs used in the combination protocols can be administered together, such as in an admixture. Where one or more anticancer drug is administered separately, the timing and schedule of administration of each drug can vary. The other therapeutic or diagnostic agents can be administered at the same time as the compounds of Formulas I and II, separately or at different times.

The compounds of Formulas I and II can also be administered in any suitable combination. Additional therapeutic agents or diagnostic agents can be administered in combination with the combination of Formulas I and II.

The compounds of the present invention can be administered with a course of hormonal therapy. The compound for hormonal therapy includes, but is not limited to, an anti-androgen and a LnRH agonist.

In clinical studies, number of lesions, tumor size, and tumor growth rate can be monitored by radiography, tomography, and, where possible, direct measurement of tumor mass. Anti-tumor effects can also be measured using molecular biology and biochemistry techniques, such as ELISA, PCR, western blotting, or immunocytochemistry.

The pharmaceutically effective amount of a composition required as a dose will depend on the route of administration, the type of cancer being treated, and the physical characteristics of the patient. The dose can be tailored to achieve a desired effect, but will depend on such factors as body surface area, weight, diet, concurrent medication and other factors which those skilled in the medical arts will recognize.

The foregoing are general guidelines only that can be expanded or altered based on, for example, disease type and grade, patient age, health status, and sex, the particular drugs used in combination, the route and frequency of administration, and experimental and clinical findings using a multidrug combination.

VII. Examples

Example 1

Compound Preparation

Compounds useful in the methods of the present invention can be prepared following the procedures set forth below.

Pyrvinium pamoate is commercially available from MP Biochemicals (Solon, Ohio). Harmol HCl is commercially available from Sigma (St. Louis, Mo.).

{2-[2-(2,5-Dimethyl-1-phenyl-1H-pyrrol-3-yl)-vinyl]-1-methyl-1,2,3,4-tetrahydro-quinolin-6-yl}-dimethyl-amine

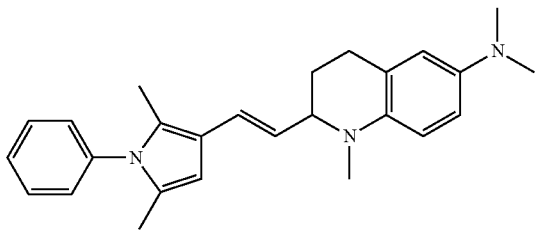 [SMILES: Cc1cc(/C=C/C2CCc3cc(N(C)C)ccc3N2C)c(C)n1-c1ccccc1]

6-Dimethylamino-2-[2-(2,5-dimethyl-1-phenyl-1H-pyrrol-3-yl)-vinyl]-1-methyl-quinolinium, pamoate salt (pyrvinium pamoate, 500 mg, 0.434 mmol) was dissolved in 10 ml of EtOH with stirring at room temperature. Sodium borohydride (67.5 mg, 1.74 mmol) was added in one portion. Stirring was continued for 3.5 hours until the reaction was judged complete by LC-MS analysis. The reaction mixture was treated with water (10 ml) and extracted three times with dichloromethane. The dichloromethane layers were consolidated and dried (sodium sulfate), filtered, and concentrated. The residue (394 mg) was purified by high-performance flash chromatography (Biotage 25+M, silica cartridge) using a gradient of 0-25% ethyl acetate in hexane over 12 column volumes to afford the {2-[2-(2,5-Dimethyl-1-phenyl-1H-pyrrol-3-yl)-vinyl]-1-methyl-1,2,3,4-tetrahydro-quinolin-6-yl}-dimethyl-amine as yellow-orange oil. Yield: 150 mg (45%).
$^1$H NMR: (400 MHz, CDCl$_3$) 1.90 (m, 1H), 1.94 (s, 3H), 1.97, (s, 3H), 2.09 (m, 1H), 2.72-2.80 (m, 2H), 2.79 (s, 6H), 2.83 (s, 3H), 3.74 (m, 1H), 5.78 (dd, J=8 Hz, 16 Hz, 1H), 6.08 (s, 1H), 6.38 (d, J=16 Hz, 1H), 6.56 (m, 2H), 6.65 (m, 1H), 7.13 (m, 2H), 7.38 (m, 3H) ESI-MS (m/z): [M+H]$^+$=386.

Dimethyl-1-phenyl-1H-pyrrol-3-yl)-ethyl]-1-methyl-1,2,3,4-tetrahydro-quinolin-6-yl}-dimethyl-amine

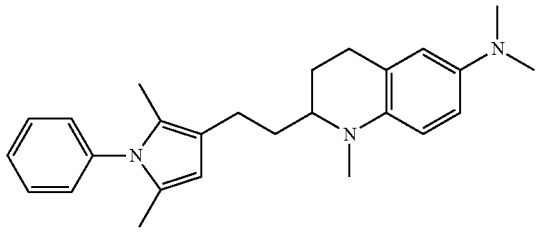 [SMILES: Cc1cc(CCC2CCc3cc(N(C)C)ccc3N2C)c(C)n1-c1ccccc1]

{2-[2-(2,5-Dimethyl-1-phenyl-1H-pyrrol-3-yl)-vinyl]-1-methyl-1,2,3,4-tetrahydro-quinolin-6-yl}-dimethyl-amine, (25 mg, 0.065 mmol) was dissolved in 4 ml methanol and combined with 10% Pd/C (13 mg). The mixture was stirred under an atmosphere of hydrogen gas (balloon) for 2 hrs or until the reaction was complete as judged by LC-MS analysis. The reaction mixture was then filtered through celite, washing with additional methanol, and the filtrate concentrated to afford an oil. The crude residue (27 mg) was purified by preparative HPLC to afford the title compound, {2-[2-(2,5-

Dimethyl-1-phenyl-1H-pyrrol-3-yl)-ethyl]-1-methyl-1,2,3,4-tetrahydro-quinolin-6-yl}-dimethyl-amine as a trifluoroacetate (TFA) salt. Yield: 23 mg (70%). $^1$H NMR: (400 MHz, CDCl$_3$) 1.59 (m, 1H), 1.85-2.03 (m, 3H), 1.91 (s, 3H), 1.97 (s, 3H), 2.33-2.52 (m, 2H), 2.67-2.92 (m, 2H), 2.94 (s, 3H), 3.11 (s, 6H), 3.36-3.42 (m, 1H), 5.78 (s, 1H), 6.53 (d, J=8 Hz, 1H), 1.83 (m, 1H), 7.08-7.39 (m, 3H), 7.32-7.46 (m, 3H) ESI-MS (m/z): [M+H]$^+$=388.

Example 2

Screening for Novel AR Antagonists

The assay below provides a method of identifying compounds that are androgen-receptor antagonists.

A library assembled by the NINDS was screened. The library consisted of 1040 FDA-approved drugs and natural products. A basic strategy to select and compare compounds from each of the primary screens was established (FIG. 1).

The transcription assay was conducted by transfecting 10 cm plates of HEK293 cells with plasmids encoding MMTV-luciferase, SV40-renilla luciferase, and native AR. These cells are useful because the limited transfection efficiency of prostate-derived cells increases the variability of the assay. The FRET assays were conducted using two independent cell lines, each stably expressing a CFP-AR-YFP fusion protein: HEK293/C-AR-Y and LAPC4/C-AR-Y. LAPC4 cells are a prostate derived line (Klein, K. A., et al., *Progression of metastatic human prostate cancer to androgen independence in immunodeficient SCID mice*. Nat Med, 1997. 3(4): p. 402-8). FRET is fluorescence resonance energy transfer between cyan and yellow fluorescent protein derivatives (CFP, YFP) that are fused to the amino and carboxyl termini of the human androgen receptor. When ligand activates the receptor, a conformational change takes place that brings the CFP and YFP into close proximity, thereby allowing FRET to occur. This spectroscopic change is detected using a fluorescence plate reader.

For the transcription assay, transfected cells were pooled before being plated into 96-well dishes with the test compounds at 10 μM. On each plate was included "no DHT" and "no treatment" controls, as well as a positive control with 1 μM OH—F. For the FRET assays, cells were directly plated into the 96-well plates with the test compounds at 10 μM. Cell and compound transfers were accomplished with a liquid handling robot. Cells were cultured for 24 hours in the presence of 10 nM DHT and the test compounds. After 24 hours, cells were either lysed by freeze-thaw (transcription assay), or fixed in 4% paraformaldehyde for reading on the FPR (FRET assays). Each compound was tested in duplicate in the initial screen.

The compounds were sorted on the basis of anti-androgen effects. In order to be selected for further analysis, a test compound had to function in both of the replicates, and in each case had to reduce the signal by at least one standard deviation from the mean of samples treated with DHT alone. This eliminated situations in which one test gave a strong response, and the replicate had none. Lastly, there must have been no evidence of cell toxicity, for the transcription assays specifically tested for renilla luciferase (which is discriminated from firefly luciferase on the basis of substrate specificity), and compounds that reduced this signal below two standard deviations were eliminated. For the FRET assays, toxic compounds were easily detected because of their effect on raw CFP and YFP signal, and compounds that reduced this signal below two standard deviations were eliminated.

Analysis of Hits from the Primary Screen.

FIG. 2 illustrates the results of the screen. The data clearly indicate that each assay system was capable of sorting compounds according to efficacy. Hits were sorted using different stringencies to determine the degree of variance from the mean that would be required to select a limited number of hits for each assay. The conformational assay, when used in either HEK293 or LAPC4 cells, achieved high selectivity using a lower stringency, whereas the transcription-based assay required higher degrees of stringency to achieve the same selectivity. Accordingly, conformational assays are less sensitive to non-specific cellular perturbation, whereas many compounds were capable of perturbing the transcriptional response.

Figure 3:
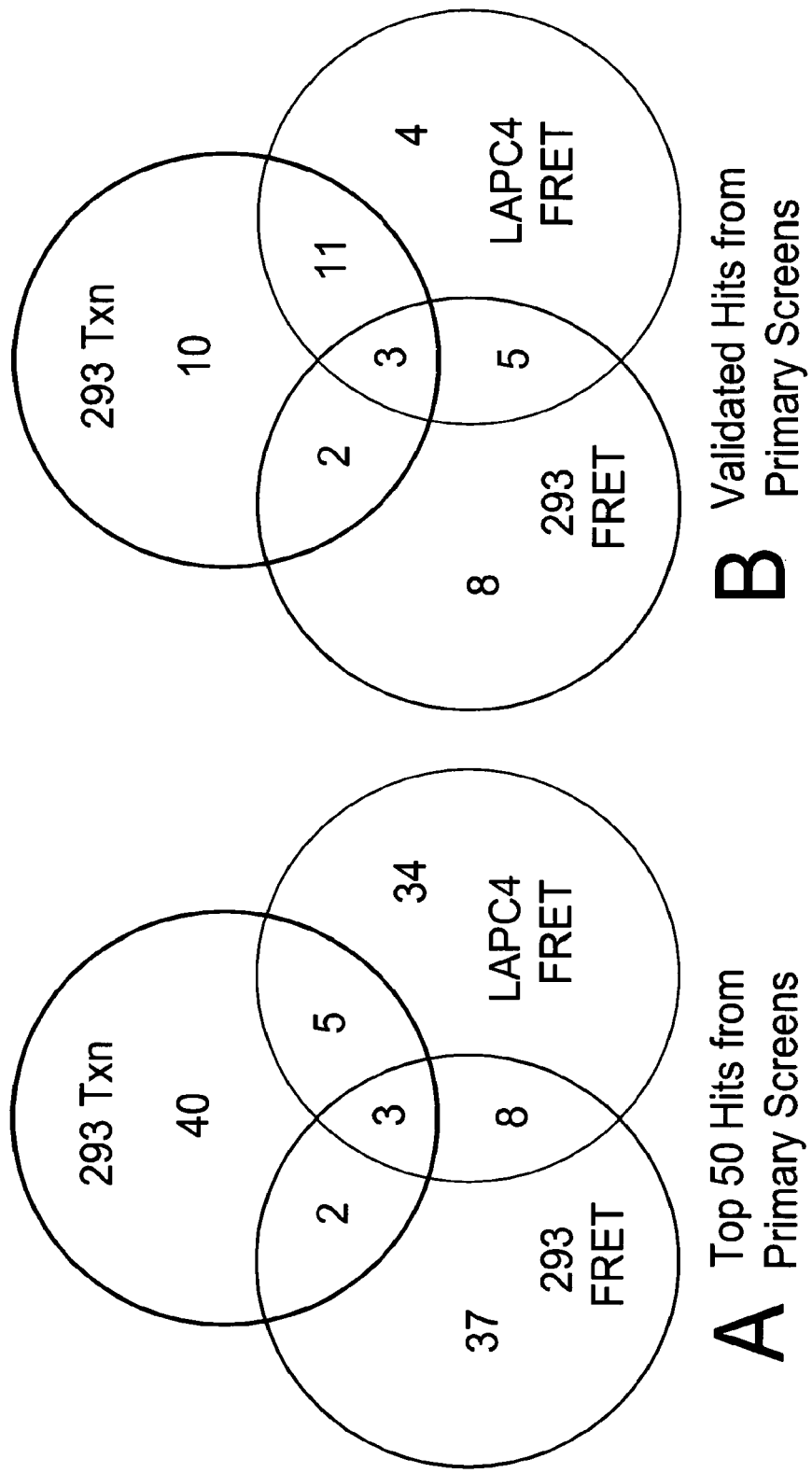
FIG. 3. Characterization of hits in primary screen. (A) Hits that scored in the primary assays were ranked according to efficacy based on the average of duplicate readings, and the top 50 from each assay was compared to the other two. In each case, a minority of compounds were shared between the assays, and most hits were unique to a particular system. (B) Validated hits were determined by detailed dose-response in the original assay used, and only compounds that exhibited pharmacologic effects were counted. These hits were then cross-compared to the other screening assays, using a dose-response. In this secondary analysis, the majority of hits from any one assay were also effective in another assay system.

The top 50 compounds identified in each primary assay were then tested in the other two assays. Among the top hits in each assay that were not included for further analysis were all known anti-androgens from the library (hydroxy-flutamide, nilutamide, cyproterone, and cyproterone acetate), and certain steroid hormones that exhibit cross-reactivity with AR at micromolar concentrations. A Venn diagram illustrates that there was modest overlap between the primary assays: approximately 20-30% of hits that scored in one assay also scored in another assay (FIG. 3).

To determine "validated" hits, the top 50 compounds were re-tested with titration studies in the original assays in which they were detected, and selected only those that exhibited a classic dose-response pattern. When validated hits from each assay were compared for activity in the others, a much higher proportion of compounds (approximately 55-82%) scored positive in at least one other assay than in the primary screen. Few compounds (3) scored positive in all three assays. This is consistent with the idea that each screening approach has the potential to identify compounds with efficacy across assays, but that it also might add a new dimension to drug discovery. Importantly, among the small number of validated hits, it was discovered that one compound in the HEK293 FRET assay, and three compounds in the LAPC4 FRET assay that initially did not meet selection criteria in the HEK293 primary transcription assay, but which showed inhibition of AR-mediated transcription upon subsequent careful analysis. Accordingly, the FRET assays can augment drug discovery vs. transcription assays alone.

Identification of Novel Anti-Androgens.

Several lead compounds survived the stringent screening protocol, and three classes with previously unrecognized anti-androgen activity: the coumarins, including warfarin, scopoletin, and esculin; harmol hydrochloride, a natural product (HH); and an FDA-approved anti-helminthic, pyrvinium pamoate (PP).

To evaluate the efficacy of pyrvinium and harmol against endogenous AR activity, each compound was tested in a dose-response assay in two prostate cancer-derived cell lines, LAPC4 (Klein, K. A., et al., *Progression of metastatic human prostate cancer to androgen independence in immunodeficient SCID mice*. Nat Med, 1997. 3(4): p. 402-8), and LNCaP (Horoszewicz, J. S., et al., *The LNCaP cell line—a new model for studies on human prostatic carcinoma*. Prog Clin Biol Res, 1980. 37: p. 115-32) that each express endogenous AR. LAPC4 cells express wild-type AR, whereas LNCaP cells, which are derived from hormone-refractory PCa, express AR with a mutation (T877A) that renders it responsive to a variety of ligands, including the antagonist hydroxy-flutamide (OH—F). Cells were transfected with two reporter plasmids, a PSA-luciferase construct (androgen responsive), and an SV40-renilla luciferase construct as an internal control. The following day, the cells were split and drugs added in the presence of 3 nM DHT. Luciferase production was measured the following day (Dual luciferase assay kit, Promega).

Figure 4:
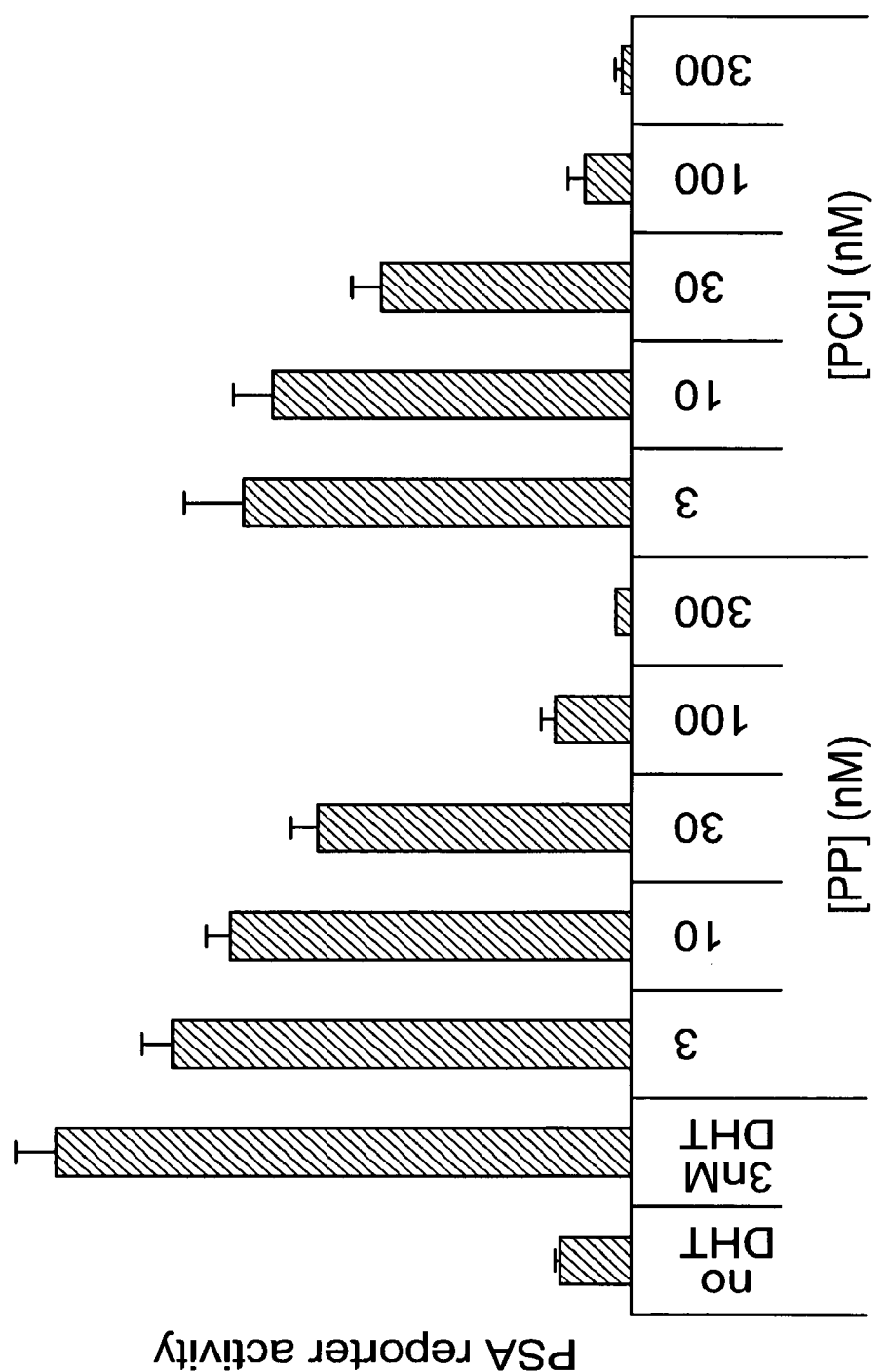
FIG. 4. Pyrvinium pamoate (PP) exhibits identical responses vs. pyrvinium chloride (PCl). Anion exchange was used to replace the pamoate salt with a chloride ion. The resulting compound, PCl, had an identical dose-response vs. the parent compound in blocking PSA reporter activity in LAPC4 cells.

No compounds had androgen activity in the absence of DHT in either the conformation or the transcription reporter assays, even at doses exceeding 10 uM. PP and HH were much more effective than the competitive antagonists OH—F and bicalutamide (BiC) at inhibiting reporter transcription (Table 1), so the anti-androgen characteristics of these compounds were studied further. Both PP and HH inhibited DHT-responsive gene expression with efficacies far superior to BiC (Table 1). To rule out the possibility that the pamoate salt of pyrvinium was mediating transcriptional inhibition, anion exchange (Dowex) was used to replace the pamoate with a chloride ion. Pyrvinium chloride was just as effective as pyrvinium pamoate (FIG. 4).

TABLE 1

IC$_{50}$ of various compounds identified in screens for novel anti-androgens.

| Compound | Activity on PSA-luciferase IC$_{50}$(nM) LNCaP | Activity on PSA-luciferase IC$_{50}$(nM) LAPC4 |
|---|---|---|
| PP | 24 | 12 |
| HH | 127 | 106 |
| OH—F | agonist | 130 |
| Casodex | 585 | 1,571 |
| Esculin | 62,159 | 831 |
| Scopoletin | 603,586 | 1,378 |
| Warfarin | 4,500 | 1,954 |
| Harmine | 1,560 | 80 |
| Harmaline | 1,190 | nd |
| Harman | 380 | nd |
| Norharman | 2,500 | nd |

PP = pyrvinium pamoate;
HH = harmol hydrochloride;
OH—F = hydroxy-flutamide;
BiC = bicalutamide.
nd = no data.

Example 3

Assay for Inhibition of an Androgen Receptor

The assay below demonstrates that the compounds identified in Example 2 inhibit endogenous androgen receptor gene expression and are not competitive antagonists.

To confirm that the effects of the lead compounds hold true for endogenous AR-regulated gene expression, quantitative RT-PCR (qRT-PCR) was used to monitor effects on a select number of androgen-responsive genes in LAPC4 and LNCaP cells. LAPC4 and LNCaP cells were grown in the presence or absence of 3 nM DHT in charcoal-stripped media, with or without the inhibitors. RNA was harvested using an RNAeasy kit (Qiagen) and reverse transcribed (MMLV-RT, Invitrogen). Real-time PCR was carried out on a 7300 Real Time PCR System (Applied Biosystems) using SYBR green as the detecting dye and Rox as the reference dye. The androgen responsive genes kalikrein 3, or PSA (KLK3) [Cleutjens, K. B., et al., *Two androgen response regions cooperate in steroid hormone regulated activity of the prostate-specific antigen promoter*. J Biol Chem, 1996. 271(11): p. 6379-88; Nelson, P. S., et al., *The program of androgen-responsive genes in neoplastic prostate epithelium*. Proc Natl Acad Sci USA, 2002. 99(18): p. 11890-5), metalloproteinase 16 (MMP16) (Nelson, P. S., et al., *The program of androgen-responsive genes in neoplastic prostate epithelium*. Proc Natl Acad Sci USA, 2002. 99(18): p. 11890-5), transmembrane protease serine 2 (TMPRSS2) (Nelson, P. S., et al., *The program of androgen-responsive genes in neoplastic prostate epithelium*. Proc Natl Acad Sci USA, 2002. 99(18): p. 11890-5; Aronin, N., et al., *Are there multiple pathways in the pathogenesis of Huntington's disease?* Philosophical Transactions of the Royal Society of London. Series B: Biological Sciences, 1999. 354 (1386): p. 995-1003; Vaarala, M. H., et al., *Expression of transmembrane serine protease TMPRSS2 in mouse and human tissues*. J Pathol, 2001. 193(1): p. 134-40), FK506-binding immunophilin 51 (FKBP51) (Nelson, P. S., et al., *The program of androgen-responsive genes in neoplastic prostate epithelium*. Proc Natl Acad Sci USA, 2002. 99(18): p. 11890-5; Amler, L. C., et al., *Dysregulated expression of androgen-responsive and nonresponsive genes in the androgen-independent prostate cancer xenograft model CWR22-R1*. Cancer Res, 2000. 60(21): p. 6134-41; Velasco, A. M., et al., *Identification and validation of novel androgen-regulated genes in prostate cancer*. Endocrinology, 2004. 145(8): p. 3913-24; Magee, J. A., et al., *Direct, androgen receptor-mediated regulation of the FKBP5 gene via a distal enhancer element*. Endocrinology, 2006. 147(1): p. 590-8), G-protein coupled receptor RDC1 homolog, or chemokine orphan receptor 1 (RDC-1) (Nelson, P. S., et al., *The program of androgen-responsive genes in neoplastic prostate epithelium*. Proc Natl Acad Sci USA, 2002. 99(18): p. 11890-5), NK homeobox family member 3 (NRx3.1) (Nelson, P. S., et al., *The program of androgen-responsive genes in neoplastic prostate epithelium*. Proc Natl Acad Sci USA, 2002. 99(18): p. 11890-5; Bieberich, C. J., et al., *Prostate-specific and androgen-dependent expression of a novel homeobox gene*. J Biol Chem, 1996. 271(50): p. 31779-82; Aboody-Guterman, K. S., et al., *Green fluorescent protein as a reporter for retrovirus and helper virus-free HSV-1 amplicon vector-mediated gene transfer into neural cells in culture and in vivo*. Neuroreport, 1997. 8(17): p. 3801-8) were all normalized to the transcription of the housekeeping ribosomal gene (RPL19). All samples were done in triplicate and separately normalized. KLK3, NRx3.1, TMPRSS2, and FKBP51 were all induced by treatment with DHT, and this induction was inhibited to varying degrees by BiC, PP, and HH. Likewise, MMP-16 and RDC-1 were repressed by treatment with DHT, and the repression was lifted to varying degrees by all of the AR inhibitors. Table 2 summarizes the results from 3 or 4 separate qRT-PCR experiments in each cell type. Two genes known to be induced by DHT in LNCaPs, NRx3.1 and TMPRSS2, were not significantly induced in LAPC4 cells. Both PP and HH were observed to readily suppress expression of several androgen-responsive genes at least as effectively as BiC (Table 2).

TABLE 2

PP and HH each inhibit gene expression mediated by endogenous AR. Both PP and HH reduced androgen-induced gene induction in a manner comparable or superior to BiC. Evaluation of androgen-repressed genes (shown in the bottom section) indicated that the inhibitors each de-repressed expression.

| | No DHT | 3 nM DHT | 3 nM DHT/ 1 µM BIC | 3 nM DHT/ 100 nM PP | 3 nM DHT/ 100 nM HH |
|---|---|---|---|---|---|
| LNCaP transcription (normalized to RPL19) | | | | | |
| KLK3 | 1 | 1.89 | 1.53 | 1.57 | 1.46 |
| Nkx3.1 | 1 | 2.00 | 1.31 | 0.78 | 1.28 |
| FKBP51 | 1 | 2.15 | 3.56 | 1.46 | 1.90 |
| TMPRSS2 | 1 | 3.70 | 2.58 | 0.92 | 1.22 |
| MMP16 | 1 | 0.61 | 0.78 | 1.57 | 1.02 |

TABLE 2-continued

PP and HH each inhibit gene expression mediated by endogenous AR. Both PP and HH reduced androgen-induced gene induction in a manner comparable or superior to BiC. Evaluation of androgen-repressed genes (shown in the bottom section) indicated that the inhibitors each de-repressed expression.

|  | No DHT | 3 nM DHT | 3 nM DHT/ 1 μM BIC | 3 nM DHT/ 100 nM PP | 3 nM DHT/ 100 nM HH |
|---|---|---|---|---|---|
| RDC1 | 1 | 0.66 | 0.66 | 0.94 | 1.22 |
| LAPC4 transcription (normalized to RPL19) | | | | | |
| KLK3 | 1 | 1.97 | 1.70 | 1.61 | 1.64 |
| Nkx3.1 | 1 | 1.08 | 1.11 | 0.77 | 1.55 |
| FKBP51 | 1 | 21.4 | 21.32 | 9.55 | 11.96 |
| TMPRSS2 | 1 | 1.13 | 1.23 | 1.90 | 1.86 |
| MMP16 | 1 | 0.71 | 2.32 | 2.92 | 4.74 |
| RDC1 | 1 | 0.63 | 2.07 | 1.22 | 2.88 |

PP and HH are Non-Competitive Antagonists.

Figure 5:
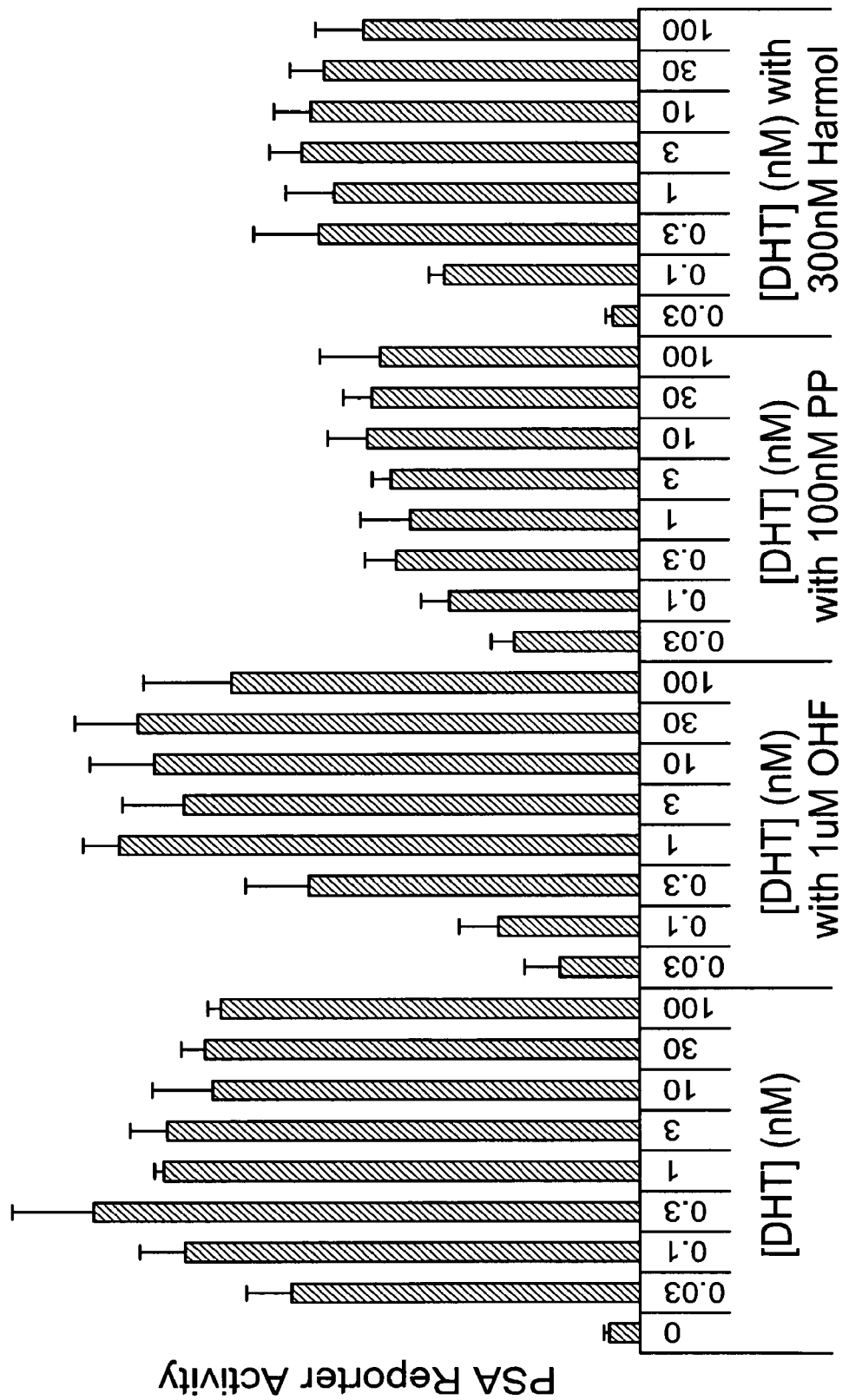
FIG. 5. PP and HH inhibit DHT-induced gene expression differently than a competitive antagonist. LNCaP cells transiently transfected with a PSA-luciferase reporter were exposed to OH—F, PP and HH. DHT was titrated. Whereas OH—F caused a modified DHT dose-response consistent with a competitive antagonist, PP and HH exhibited a pattern consistent with a non-competitive antagonist.

As a first step to determine whether PP and HH function as competitive or noncompetitive antagonists of AR, DHT was titrated in LNCaP cells transiently transfected with a PSA-luciferase reporter, and treated with a moderate dose of each inhibitor. DHT overcame the inhibitory effect of OH—F, producing maximal activation. By contrast, both PP and HH inhibited maximal DHT-induced activation, despite very high final DHT concentrations (FIG. 5). This was consistent with activity as non-competitive antagonists.

Example 4

Synergistic Behavior of PP, HH and BiC

The presence of synergy in the use of PP, HH and BiC as androgen receptor antagonists is confirmed using the procedure below.

The existence of synergy between the lead compounds and BiC was tested for using LAPC4 and LNCaP cells. When added in various combinations to LNCaP and LAPC4 cells transfected with the PSA-luciferase, both PP and HH synergized with each other, and with BiC (Table 3). Synergism can be defined as a combination index of less than one, using the non-exclusive assumption described by Chou et al. (Chou, T. C. and P. Talalay, Quantitative analysis of dose-effect relationships: the combined effects of multiple drugs or enzyme inhibitors. Adv Enzyme Regul, 1984. 22: p. 27-55). The synergy between PP, HH, and BiC is indicates that they function by distinct mechanisms.

TABLE 3

Synergy between PP, HH and BiC. Dose response curves were carried out with the inhibitors in the indicated ratios, using 3 nM DHT to activate transcription from PSA-Luciferase in the indicated cell types (LNCaP or LAPC4). The expected IC50 value is reported for the first drug indicated in the combination. The Combination Index is a calculated measure of "synergy" based on Chou et al. (1984); numbers lower than one indicate synergy.

| Combination | Cell Type | Expected IC$_{50}$ (nM) | Actual IC$_{50}$ (nM) | Combination Index at f50 |
|---|---|---|---|---|
| PP:HH 1:1 | LNCaP | 9.27 | 8.27 | 0.54 |
| PP:HH 1:1 | LAPC4 | 7.83 | 4.57 | 0.28 |
| PP:BIC 1:1 | LNCaP | 18.47 | 12.23 | 0.33 |
| PP:BIC 1:1 | LAPC4 | 18.25 | 0.64 | 0.02 |
| HH:BIC 1:1 | LNCaP | 78.05 | 31.85 | 0.21 |

TABLE 3-continued

Synergy between PP, HH and BiC. Dose response curves were carried out with the inhibitors in the indicated ratios, using 3 nM DHT to activate transcription from PSA-Luciferase in the indicated cell types (LNCaP or LAPC4). The expected IC50 value is reported for the first drug indicated in the combination. The Combination Index is a calculated measure of "synergy" based on Chou et al. (1984); numbers lower than one indicate synergy.

| Combination | Cell Type | Expected IC$_{50}$ (nM) | Actual IC$_{50}$ (nM) | Combination Index at f50 |
|---|---|---|---|---|
| HH:BIC 1:1 | LAPC4 | 142.1 | 28.33 | 0.1 |
| PP:HH 1:10 | LNCaP | 26.79 | 2.56 | 0.08 |
| PP:BIC 1:10 | LNCaP | 27.21 | 0.4 | 0.01 |
| PP:BIC 1:30 | LNCaP | 27.69 | 10.25 | 0.44 |
| PP:BIC 1:100 | LNCaP | 27.09 | 2.38 | 0.32 |
| PP:OHF 1:1 | LAPC4 | 7.56 | 5.79 | 0.39 |
| Harmol:OHF | LAPC4 | 93.06 | 66.18 | 0.38 |

Example 5

Growth Inhibition by PP and HH

The procedures set-forth below were used to determine whether PP and HH would affect the androgen-dependent proliferation of LAPC4 and LNCaP cells in cell culture, as well as the androgen-independent growth of LN-AR cells that over-express AR, and which are a model of "androgen independent" prostate cancer.

Figure 6:
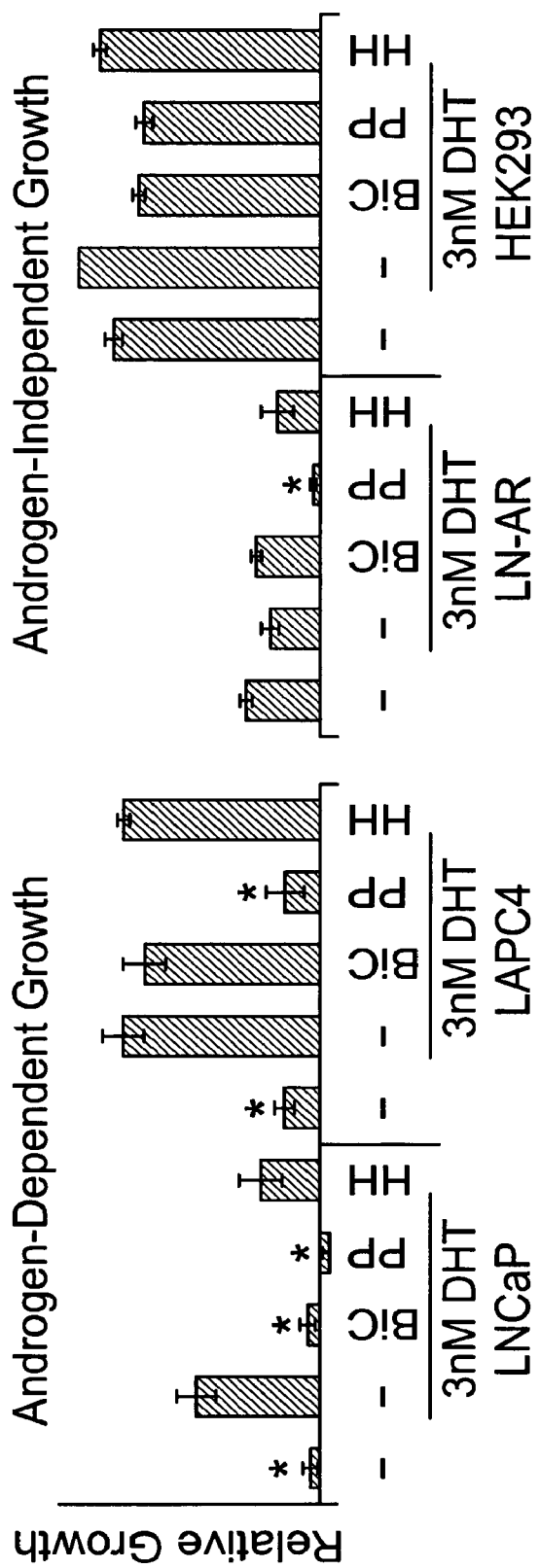
FIG. 6. PP and HH inhibit androgen-induced cell proliferation. PP, HH, and BiC were compared for their ability to inhibit androgen dependent and independent growth in several cultured cell lines: LNCaP, LAPC4, LN-AR (a line that exhibits androgen-independent growth), and HEK293 cells. PP and HH each exhibited growth-inhibitory properties in LNCaP cells, whereas HH was not effective in LAPC4 cells. Neither compound exhibited non-specific growth inhibition of HEK293 cells. Importantly, PP blocked growth of "hormone refractory" LN-AR cells. Asterisk (*)=p<0.005.

LN-AR cells were created by retroviral infection of a high-expressing AR vector into LNCaP cells, and proliferate independent of androgen in cell culture, unlike their parental line (Chen, C. D., et al., *Molecular determinants of resistance to antiandrogen therapy*. Nat Med, 2004. 10(1): p. 33-9). HEK293 cells were used as a control. Cells were transferred to charcoal-stripped media two days before they were split and plated in quadruplicate at a density of approximately 20,000 cells/well in 48-well plates. The following day, medium with or without 3 nM DHT was added to the cells with or without PP (100 nM), HH (100 nM), or BiC (1 μM). Media were changed every day, using a single preparation to ensure consistent compound concentrations. Proliferation was determined by measuring the DNA content of the cells in each well. Each day, the cells in four wells were fixed in 100% cold methanol, followed by staining for 5 min at RT with 0.2 ng/mL 4',6-diamidino-2-phenylindole (DAPI) in PBS. The cells were washed once in PBS, then read on a fluorescence plate reader using 365/439 excitation/emission wavelengths. LAPC4 and LNCaP cells proliferated to a much greater degree in the presence of DHT, while LN-AR cells proliferated in the presence and absence of DHT. PP was the only compound able to inhibit the growth of all four cell lines after seven days, while HH and BiC only inhibited significantly the growth of LNCaP cells. Control HEK293 cells were not significantly affected by any of the compounds, suggesting that none of them has non-specific growth-inhibitory effects. PP and HH worked at least as well as BiC to block androgen-induced proliferation (FIG. 6).

Example 6

Pharmacokinetics and Toxicity of Compounds in Mice

Anti-androgen activity of PP and HH in mice were determined using the procedure set forth below.

Wild-type FVB mice were given a single intraperitoneal injection of either PP or HH. Serum samples were obtained at fixed time intervals, and the drug levels determined by mass spectrometry. These results indicated that HH was rapidly cleared. PP exhibited a prolonged half-life indicating that it could be a suitable therapy (Table 4). Toxicity of PP was tested using various doses ranging from 0.1 to 10 mg/kg. 10 mg/kg was toxic, while the mice tolerated 5 mg/kg.

TABLE 4

Pharmacokinetics of PP vs. HH. Mice were given a single IP injection or PO dose of PP or HH at 5 mg/kg. Serum samples were drawn at the indicated time points, and blood levels measured using mass spectrometry.

|    | 0.25 hr | 1 hr | 6 hr | 24 hr |
|----|---------|------|------|-------|
| Plasma [PP] (ng/mL) | | | | |
| PO | 40.2 | 13.5 | nd | nd |
| IP | 57.2 | 19.7 | 15.9 | 6.9 |
| Plasma [HH] (ng/mL) | | | | |
| PO | 6.7 | nd | nd | nd |
| IP | 32.3 | 5.0 | nd | nd |

PP Synergizes with BiC In Vivo to Cause Prostate Atrophy.

As a positive control, one cohort was castrated four weeks prior to tissue recovery, one cohort was untreated, and the other cohorts were treated either with 1 mg/kg PP, 100 mg/kg BiC, or PP/bicalutamide (BiC) in combination. Animals were treated 5 times per week for four weeks. At the end of the study period, animals were sacrificed and prostate tissue weighed. After weighing, the tissue was divided in half for pathological and genetic studies. BiC treatment decreased prostate tissue size by 35% (p<0.003). Treatment with PP:BiC caused a further reduction by 63% that was highly significant vs. the effect of BiC alone (P<0.0005). PP alone did not produce a statistically significant effect. (FIG. 7).

PP Synergizes with BiC In Vivo to Inhibit Androgen-Dependent Prostate Gene Expression.

To evaluate the effect of PP and PP:BiC on androgen-dependent gene expression in the prostate, total RNA was prepared from half of the prostate glands isolated in the in vivo trial. RT-PCR was carried out, and gene expression was determined relative to RPL19, an endogenous prostate gene that is completely androgen unresponsive (E. Bolton, K. R. Yamamoto: unpublished data). Five androgen-responsive genes that are expressed throughout all lobes of the mouse prostate were evaluated. In each case, it was observed that PP and BiC reduced gene expression significantly, but their combination was superior. In most cases, the combination approached that of castrated animals (FIG. 8). Taken together with the preceding experiment, PP exerts anti-androgen effects, and synergy with BiC as an anti-androgen in vivo.

Example 7

Effects of PP, THP, and BiC on the Mouse Prostate

10 FVB male mice (12 wk) were treated with vehicle, 1 mg/kg pyrvinium pamoate (PP), 100 mg/kg bicalutamide (BiC), 2 mg/kg THP, 20 mg/kg, or a combination of 2 mg/kg THP and 100 mg/kg BiC for 5 weeks, daily, M-F dosing. A cohort of mice were castrated as a positive control.

Figure 11:
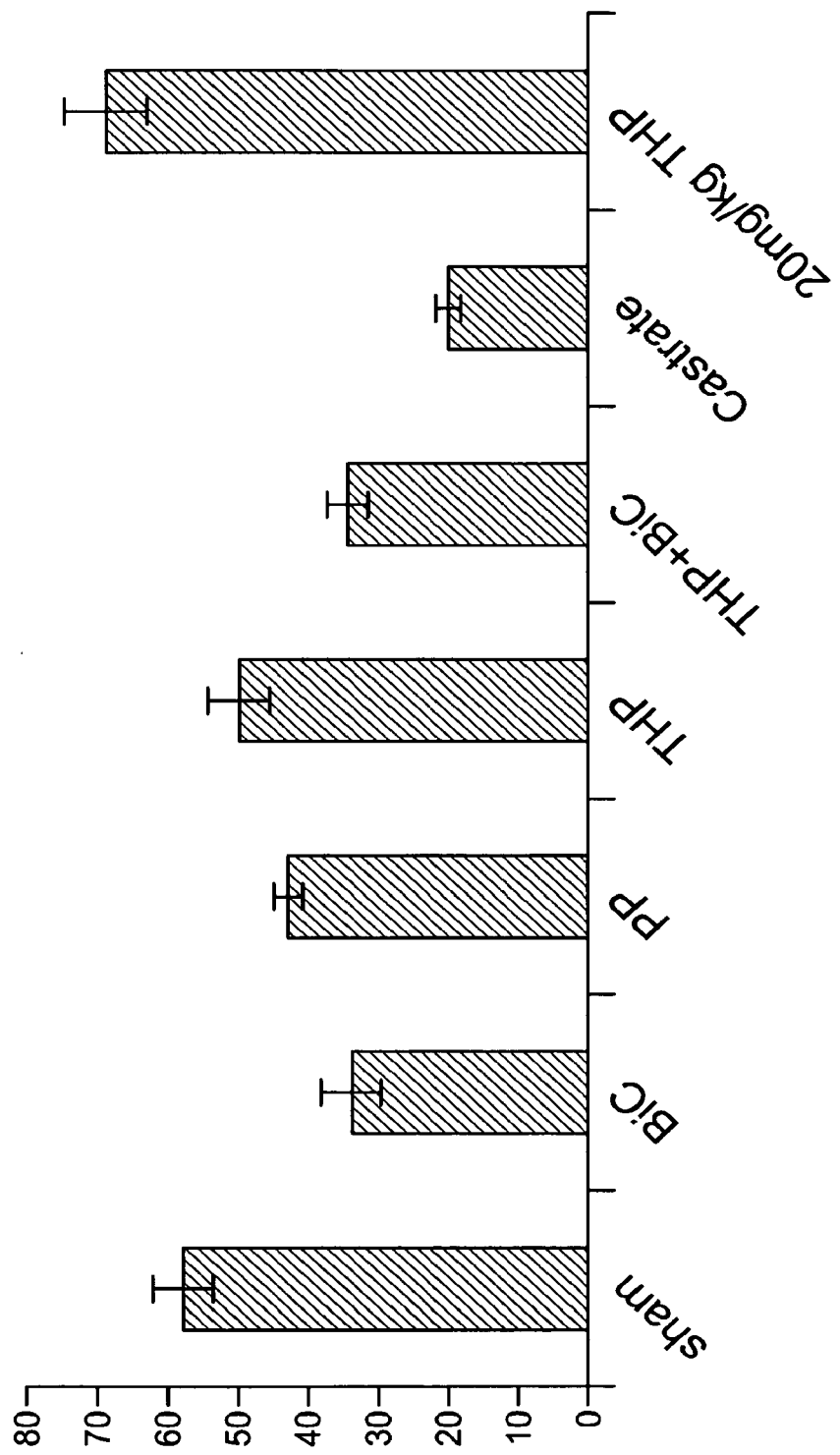
FIG. 11. Change in prostate wet weight after treatment with BiC, PP, THP+BiC, or castration.

Treatment with BiC, PP, THP+BiC, or castration caused a significant (by analysis of variance) decrease in prostate wet weight. 20 mg/kg THP caused an abnormal milky appearance of the prostate, though it did not reduce overall wet weight (FIG. 11)

Figure 12:
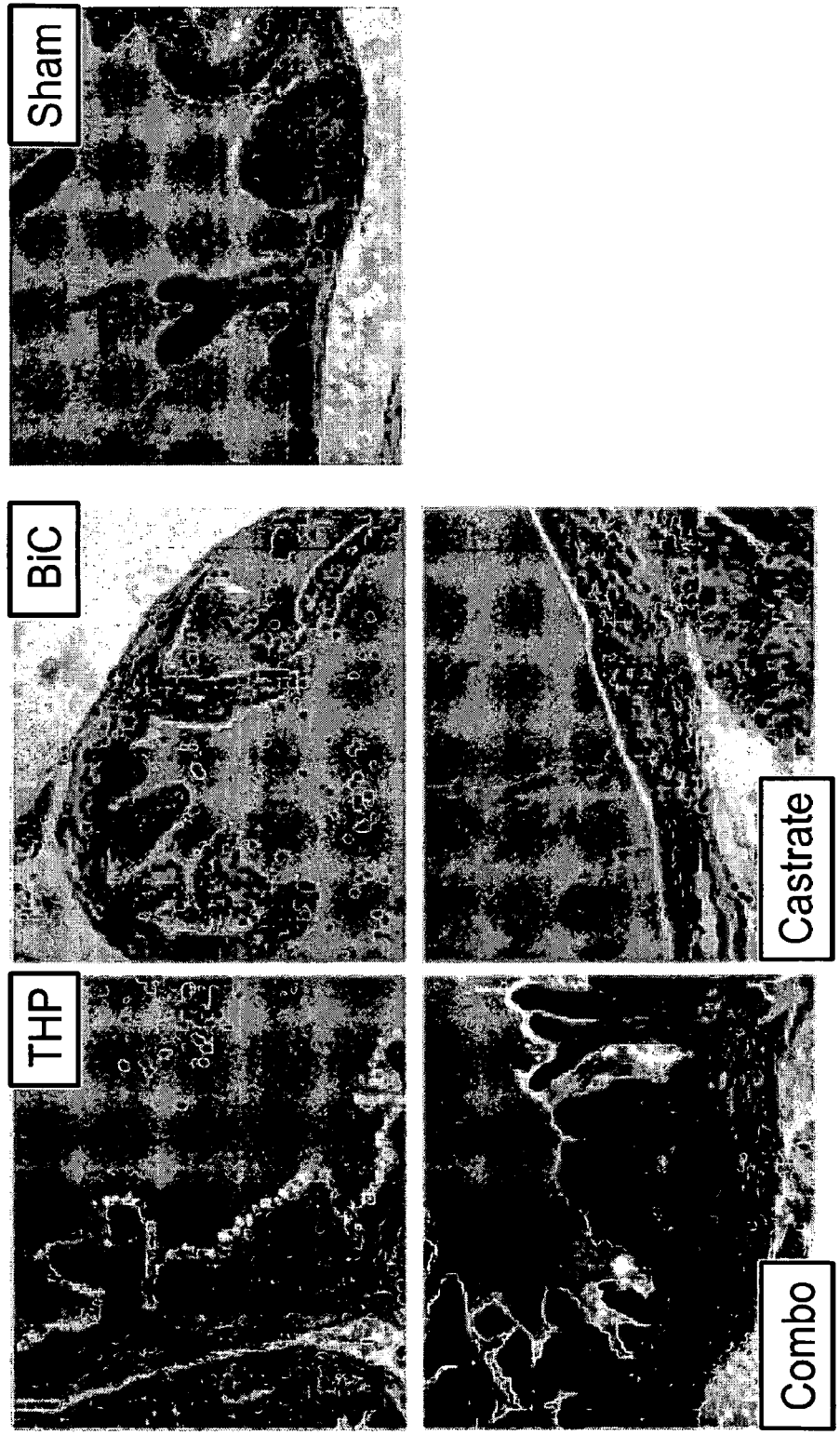
FIG. 12. Histology of mice dorsal prostate after treatment with THP, BiC, THP+BiC, or castration.

Mice treated with THP or BiC alone had modest atrophy in the dorsal prostate (by histological examination) as well as other lobes, whereas a combination of the two caused severe atrophy similar to that caused by castration (FIG. 12).

For quantitative PCR, RNA was isolated from mouse prostates and reverse-transcribed. The expression of several androgen-regulated genes, of which a subset is shown (FIG. 13), was determined by using QPCR and normalizing to the expression of the housekeeping gene RPL19. While 2 mg/kg treatment of THP had modest effects, 20 mg/kg THP treatment significantly decreased the transcription of many androgen regulated genes in the prostate.

Example 8

Efficacy of THP, THP:BiC, and SHP Against AR Transcription in LAPC4 Cells

Figure 14:
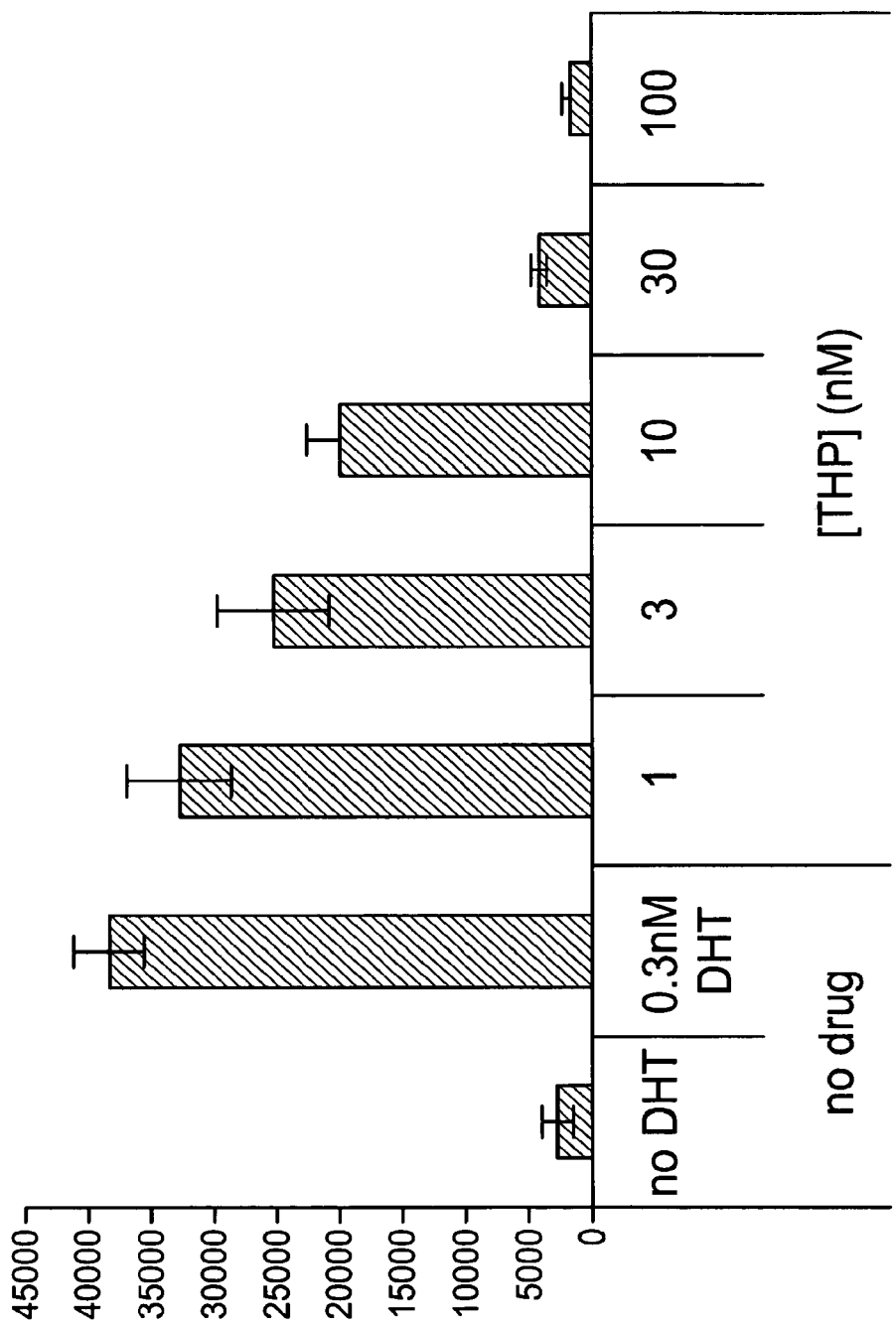
FIG. 14. THP efficacy against AR transcription in LAPC4 cells.

LAPC4 cells, a prostate cancer cell line that expresses native androgen receptor, were transfected with a PSA-luciferase reporter, and a CMV-renilla luciferase control. Cells were treated with DHT and increasing amounts of tetrahydropyrvinium (THP), as indicated in FIG. 14. Normalized luciferase activity was determined, which demonstrates strong inhibition of androgen receptor-mediated transcription by tetrahydropyrvinium.

In a separate experiment, cells were treated with DHT or a titration of a 1:30 tetrahydropyrvinium/bicalutamide combination to test for synergy. The combination of the two drugs exceeded the transcriptional inhibition predicted by an additive effect, indicating synergistic inhibition of the androgen receptor (FIG. 15).

Figure 16:
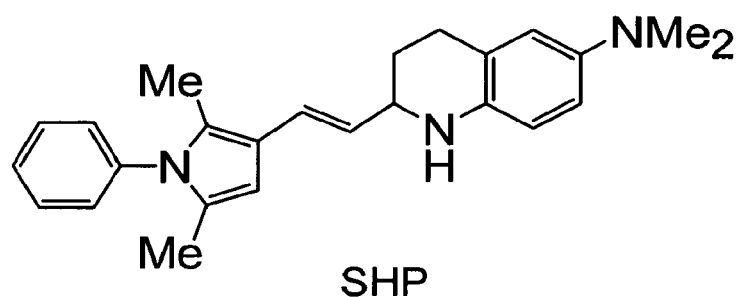
FIG. 16. THP and SHP efficacy against PSA-luciferase AR-responsive promoter in LAPC4 cells.

In a second separate experiment, the activity of SHP and THP against PSA-luciferase AR-responsive promoter was determined (FIG. 16).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of inhibiting the androgen receptor, the method comprising:
   administering to a patient in need thereof, a therapeutically effective amount of a compound of Formula I:

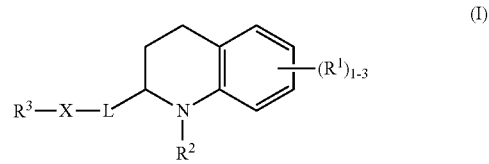

(I)

wherein
   each $R^1$ is independently selected from the group consisting of hydrogen, $C_{1-6}$ alkyl, $C_{2-6}$ alkenyl, $C_{2-6}$ alkynyl, $C_{1-6}$ alkoxy, $-SR^4$, $-NR^4R^5$, cycloalkyl, heterocycloalkyl, aryl and heteroaryl;
   $R^2$ is selected from the group consisting of hydrogen, $C_{1-6}$ alkyl, $C_{1-6}$ alkyl-OH, $C_{2-6}$ alkenyl and $C_{2-6}$ alkynyl;
   $R^3$ is aryl, optionally substituted with from 1 to 3 $R^6$ groups;

$R^4$ and $R^5$ are each independently selected from the group consisting of hydrogen, $C_{1-6}$ alkyl, $C_{2-6}$ alkenyl and $C_{2-6}$ alkynyl; or $R^4$ and $R^5$ are combined with the nitrogen to which they are attached to form a heterocyclic ring having from 5 to 7 ring members and from 1 to 3 heteroatoms each independently selected from the group consisting of N, O and S;

each $R^6$ is independently selected from the group consisting of H, $C_{1-6}$ alkyl, $C_{2-6}$ alkenyl, $C_{2-6}$ alkynyl and $C_{1-6}$ alkoxy;

L is a linker selected from the group consisting of $C_{1-6}$ alkylene, $C_{2-6}$ alkenylene, $C_{2-6}$ alkynylene and $C_{3-6}$ cycloalkylene;

X is a heteroaryl ring having from 5 to 6 ring members and from 1 to 3 heteroatoms each independently selected from the group consisting of N, O and S, optionally substituted with from 1 to 3 $R^8$ groups;

each $R^8$ is independently selected from the group consisting of H, $C_{1-6}$ alkyl, $C_{2-6}$ alkenyl, $C_{2-6}$ alkynyl and $C_{1-6}$ alkoxy;

and salts, hydrates and prodrugs thereof, thereby inhibiting the androgen receptor.

2. The method of claim 1, wherein the compound is selected from the group consisting of

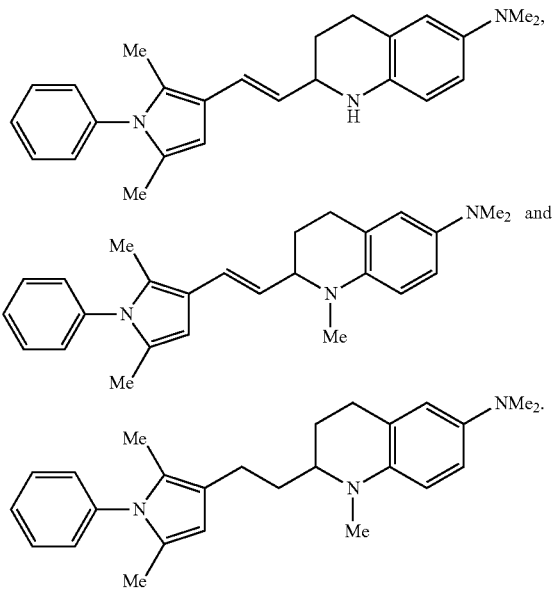

3. The method of claim 1, wherein the salt forms comprise a counterion selected from the group consisting of pamoate, chloride, bromide, succinate, maleate and acetate.

4. The method of claim 1, wherein the method of inhibiting treats a disease selected from the group consisting of prostate cancer, ovarian cancer, hepatocellular carcinoma, acne vulgaris, endometriosis, acanthosis nigricans, hypertrichosis, breast cancer, precocious puberty, polycystic ovary syndrome, benign prostatic hyperplasia, alopecia, hirsutism and hypersexuality/paraphilia.

5. The method of claim 4, wherein the disease is prostate cancer.

6. The method of claim 5, wherein the disease is primary prostate cancer.

7. The method of claim 5, wherein the disease is hormone refractory prostate cancer.

8. The method of claim 4, wherein the administration is via topical, oral, intravenous, intradermal, intramuscular or parenteral administration.

9. The method of claim 4, wherein the disease is alopecia and the administration is topical.

10. The method of claim 1, wherein the compound of Formula I is administered with a course of hormonal therapy, wherein the compound for hormonal therapy is selected from the group consisting of an anti-androgen and a LnRH agonist.

11. The method of claim 10, wherein the compounds are administered separately.

12. The method of claim 10, wherein the compounds are admixed.

13. The method of claim 10, wherein the compounds are administered at the same time.

14. The method of claim 10, wherein the compounds are administered at different times.

15. The method of claim 10, wherein the compound of Formula I is administered in combination with a therapeutically effective amount of a compound selected from the group consisting of docetaxel, paclitaxel, bicalutamide, flutamide, hydroxyflutamide, nilutamide, spionolactone, cyproterone acetate, ketoconazole, finasteride and dutasteride.

16. The method of claim 10, wherein the compound of Formula I is administered in combination with a therapeutically effective amount of a coumarin.

17. The method of claim 10, wherein the compound of Formula I is administered in combination with a therapeutically effective amount of bicalutamide.

* * * * *